United States Patent
Itahana et al.

(10) Patent No.: US 7,250,429 B2
(45) Date of Patent: Jul. 31, 2007

(54) AMINOMETHYL-SUBSTITUTED THIAZOLOBENZIMIDAZOLE COMPOUNDS

(75) Inventors: Hirotsune Itahana, Tsukuba (JP); Jiro Fujiyasu, Tsukuba (JP); Satoshi Hayashibe, Tsukuba (JP); Toshihiro Watanabe, Tsukuba (JP); Masamichi Okada, Tsukuba (JP); Takashi Toya, Tsukuba (JP)

(73) Assignee: Astellas Pharma Inc., Tokyo (JP)

( * ) Notice: Subject to any disclaimer, the term of this patent is extended or adjusted under 35 U.S.C. 154(b) by 386 days.

(21) Appl. No.: 10/508,329

(22) PCT Filed: Mar. 19, 2003

(86) PCT No.: PCT/JP03/03348

§ 371 (c)(1),
(2), (4) Date: Sep. 20, 2004

(87) PCT Pub. No.: WO03/078441

PCT Pub. Date: Sep. 25, 2003

(65) Prior Publication Data

US 2005/0148642 A1 Jul. 7, 2005

(30) Foreign Application Priority Data

Mar. 20, 2002 (JP) .............................. 2002-077431

(51) Int. Cl.
*A61K 31/429* (2006.01)
*C07D 513/04* (2006.01)

(52) U.S. Cl. .................... 514/366; 548/151; 548/302.1

(58) Field of Classification Search ................ 548/151, 548/150, 302.1; 514/366
See application file for complete search history.

(56) References Cited

FOREIGN PATENT DOCUMENTS

| | | | |
|---|---|---|---|
| EP | 1 059 090 A1 | 12/2000 |
| EP | 1 167 369 A1 | 1/2002 |
| EP | 1 205 187 A1 | 5/2002 |
| JP | 2000-351782 A | 12/2000 |
| WO | WO 99/44639 A1 | 10/1999 |
| WO | WO 00/59913 A1 | 10/2000 |
| WO | WO 01 08705 A1 | 8/2001 |

*Primary Examiner*—Golam Shameem
*Assistant Examiner*—Karen Cheng
(74) *Attorney, Agent, or Firm*—Sughrue Mion, PLLC

(57) ABSTRACT

This invention relates to the provision of novel aminomethyl-substituted thiazolobenzimidazole derivatives represented by the following general formula (I) or a salt thereof.

The aforementioned derivative or a salt thereof has a metabotropic glutamate receptor action and excellent oral activity and is therefore useful as a medicament.

(I)

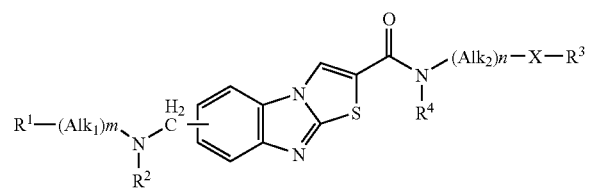

(In the formula, $R^1$: an oxygen-containing saturated hetero ring or the like, $Alk_1$: a lower alkylene, m: 0 or 1, $Alk_2$: a lower alkylene which may be substituted with oxo group, n: 0 or 1, X: a bond, O, S or $NR^5$, $R^3$: H or the like, and $R^2$, $R^4$, $R^5$, $R^6$ and $R^7$: the same or different from one another and each represents H or the like.

Provided that $R^3$ does not represent a lower alkyl or a halogeno-lower alkyl when X is a bond and n is 1. Also, $R^4$ represents a group other than Me when m is 1, $R^1$ is OH or OMe and $Alk_1$ is a $C_{1-3}$ alkylene, and further 1) when X is a bond, n is 1 and $R^3$ is H, or 2) when X is a bond, n is 0 and $R^3$ is cyclohexane.)

3 Claims, No Drawings

# AMINOMETHYL-SUBSTITUTED THIAZOLOBENZIMIDAZOLE COMPOUNDS

CROSS REFERENCE TO RELATED APPLICATIONS

This application is a U.S. National Phase application under 35 U.S.C. § 371 of PCT Application No. PCT/JP03/03348, filed Mar. 19, 2003, which claims priority under 35 U.S.C. 119 to Japanese Application No. 2002-77431 filed on Mar. 20, 2002.

TECHNICAL FIELD

This invention relates to novel aminomethyl-substituted thiazolobenzimidazole derivatives or a salt thereof, which has high safety and is useful as a medicament.

BACKGROUND OF THE INVENTION

Glutamic acid acts as a neurotransmitter in the mammalian central nervous system (Mayer M. L. and Westbrook G. L., *Prog. Neurobiol.*, 28 (1987) 197-276). By the recent studies, importance of glutamic acid in the higher order cranial nerve function has been revealed. Glutamic acid is released from the nerve ending and regulates activity of nerve cells or release of a neurotransmitter, via glutamate receptors which are present in the postsynaptic membrane or nerve ending. Based on various pharmacological and physiological studies, glutamate receptors are currently classified roughly into two categories. One of them is ionotropic receptor and the other is metabotropic receptor (Hollmann M and Heinemann S., *Annu. Rev. Neurosci.*, 17 (1994) 31-108).

Based on the molecular biological studies, it has been reported that the metabotropic glutamate receptor (to be referred sometimes to as mGluR hereinafter) exists so far in at least eight different subtypes of from mGluR 1 to mGluR 8. The mGluR is classified into a group of receptors (group I: mGluR 1 and mGluR 5) which accelerate production of inositol triphosphate (IP3) and incorporation of calcium ions into cells, by coupling with phospholipase C via G protein, and other groups of receptors (group II: mGluR 2 and mGluR 3, group III: mGluR 4, mGluR 6, mGluR 7 and mGluR 8) which inhibit production of cAMP by coupling with Gi protein. These receptors show different intracerebral distributions from one another, for example, mGluR 6 does not exist in the brain but exists only on the retina, so that it is considered that each receptor is taking each own different physiological role (Nakanishi S., *Neuron*, 13 (1995) 1031-1037).

Compounds which are selective for the mGluR in comparison with the ionotropic receptor have so far been reported (Hayashi Y. et al., *Br. J. Pharmacol.*, 107 (1992) 539-543; Hayashi Y. et al., *J. Neurosci.*, 14 (1995) 3370-3377), and relationships between the mGluR and various morbid states of diseases have been reported as the following cases (1) to (6), based on the studies carried out using these compounds.

(1) Epilepsy is induced by the administration of an mGluR agonist (1S,3R)-1-aminocyclopentane-1,3-dicarboxylic acid (to be referred to as (1S,3R)-ACPD hereinafter) (Tizzano J. P. et al., *Neurosci. Lett.*, 162 (1993) 12-16; McDonald J. W. et al., *J. Neurosci.*, 13 (1993) 4445-4455). In addition, the efficacy of (S)-4-carboxy-3-hydroxyphenylglycine (to be referred to as (S)-CHPG hereinafter), which is an antagonist of mGluR 1 and also an agonist of mGluR 2, in various epilepsy models has been reported (Dalby, N. O. & Thomsen, C. J., *J. Pharmacol. Exp. Ther.*, 276 (1996) 516-522).

(2) Participation of mGluR in the transmission of pain sensation into spinal posterior horn nerve cells has been confirmed by electro-physiological tests (Young, M. R. et al., *Neuropharmacology*, 33 (1994) 141-144; ibid., 34 (1995) 1033-1041). In addition, it has been reported that the (S)-CHPG has an action to delay avoiding reaction of thermal and mechanical pain sensation stimulation (Young, M. R. et al., *Br. J. Pharmacol.*, 114 (1995) 316P).

(3) It has been reported that when the (1S,3R)-ACPD or an mGluR agonist (RS)-3,5-dihydroxyphenylglycine (to be referred to as 3,5-DHPG hereinafter) is administered in a trace amount or systemically to the cerebral parenchyma of mouse or rat, it causes nerve cell death accompanied by spasm (Lipartit, M. et al., *Life Sci.*, 52 (1993) PL 85-90; McDonald, J. W. et al., *J. Neurosci.*, 13 (1993) 4445-4455; Tizzano, J. P. et al., *Neuropharmacology*, 34 (1995) 1063-3067). It is considered that this is a result of the activation of mGluR 1 and mGluR 5.

(4) It is well known that chronic administration of benzodiazepine forms its dependency. It has been reported that metabolic turnover of inositol-phospholipid increases by (1S,3R)-ACPD via mGluR, on the second day and third day after 7 days of continuous administration of benzodiazepine, and it has been suggested that mGluR is taking a role in the expression of benzodiazepine withdrawal syndrome (Mortensen, M. et al., *J. Pharmacol. Exp. Ther.*, 274 (1995) 155-163).

(5) It has been reported that N-methyl-4-phenyl-1,2,3,6-tetrahydropyridine-induced substantia nigra dopamine nerve cell death is inhibited by the ventricular administration of a mGluR group I antagonist 1-aminoindane-1,5-dicarboxylic acid (Aguirre, J. A. et al., *Neuroreport.* 12 (2001) 2615-2617).

(6) It has been reported that an antagonist of mGluR 1 inhibits protein extravasation outside of dural blood vessels caused by an electric stimulus of trigeminal ganglion (WO 01/32632).

That is, the above reports show that compounds which act upon mGluR 1 are useful in epilepsy, pain, nerve cell death inhibition, benzodiazepine withdrawal syndrome and migraine.

Also, since the efficacy of a mGluR 1 antagonist has been confirmed in a rat cerebral infarction model, it is considered that the mGluR 1 antagonist is useful as a preventive or therapeutic agent for cerebral infarction (Patent Reference 1).

In addition, since it has been confirmed that a mGluR 1 antagonist improves reduction of pain threshold in neuropathic pain model, it is also useful as an agent for treating neuropathic pains such as a pain after shingles, a pain accompanied by diabetic neuropathy, a carcinomatous pain, a postoperative chronic pain and the like (Patent Reference 2).

As compounds having mGluR 1 antagonism, thiazolobenzimidazole derivatives are disclosed in the aforementioned Patent References 1,2 and 3 and Patent Reference 4.

However, the thiazolobenzimidazole derivatives disclosed in the aforementioned Patent References 1, 3 and 4 are compounds which were found aimed at cerebral infarction as the principal indication whose main administration route is parenteral administration.

In addition, it is reported in the Patent Reference 2 that thiazolobenzimidazole derivatives in which the benzene ring moiety of thiazolobenzimidazole ring is substituted with substituted or unsubstituted amino group show a neuropathic pain therapeutic effect by oral administration.
[Patent Reference 1]
PCT International Publication Pamphlet WO 99/44639
[Patent Reference 2]
PCT International Publication Pamphlet WO 01/08705
[Patent Reference 3]
PCT International Publication Pamphlet WO 00/59913
[Patent Reference 4]
JP-A-2000-351782

Problems that the Invention is to Solve

The object of the invention is to provide clinically useful novel thiazolobenzimidazole derivatives and a salt thereof, as metabotropic glutamate receptor antagonists having excellent oral activity.

Also, though the compounds of the aforementioned Patent Reference 2 have an oral activity, they also have a carcinogenic action, because it has been confirmed by this firm's studies that they have gene mutagenicity. It is considered that this gene mutagenicity is expressed by a structural characteristic in that they have an aniline amino group, so that compounds having an aniline amino group have a disadvantage in that they cannot be used in clinical tests as a medicament even in case that they have an oral activity.

The present inventors have conducted intensive studies with the aim of solving the aforementioned problems, and accomplished the invention by finding that the aminomethyl-substituted thiazolobenzimidazole derivatives of the invention are compounds which have a strong oral activity as a metabotropic glutamate receptor antagonist and are clinically useful because of no mutagenicity.

In this connection, the compounds of the invention are compounds which are not illustratively disclosed in the aforementioned Patent References 1 and 3, in terms that they have an oxygen-containing saturated hetero ring, a sulfur-containing saturated hetero ring or the like, or an aminomethyl group substituted with an alkyl substituted with such a saturated hetero ring, as a substituent group on the benzene ring moiety of thiazolobenzimidazole ring.

Accordingly, the invention relates to aminomethyl-substituted thiazolobenzimidazole derivatives represented by the following general formula (I) or a salt thereof and a medicament which uses the same as the active ingredient.

Illustratively, it relates to an aminomethyl-substituted thiazolobenzimidazole derivative represented by the following general formula (I) or a salt thereof

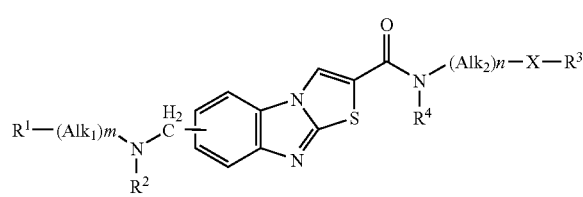

(I)

(wherein signs in the formula mean as follows;
$R^1$: an oxygen-containing saturated hetero ring- which may be substituted, a sulfur-containing saturated hetero ring- which may be substituted, a cycloalkyl which may be substituted, —O—$R^6$ or —S—$R^7$,
Alk1: a lower alkylene,
m: 0 or 1,
Alk2: a lower alkylene which may be substituted with oxo group,
n: 0 or 1,
X: a bond, O, S or $NR^5$,
$R^3$: H, a lower alkyl, a halogeno-lower alkyl, a lower alkenyl, a lower alkynyl, a cycloalkyl which may be substituted, cyano or a saturated hetero ring-, and $R^2$, $R^4$, $R^5$, $R^6$ and $R^7$: the same or different from each other and each represents H or lower alkyl, with the proviso that $R^3$ does not represent a lower alkyl or a halogeno-lower alkyl when X is a bond and n is 1, and that $R^4$ represents a group other than methyl when m is 1, $R^1$ is OH or a methoxy and Alk1 is a $C_{1-3}$ alkylene, and further 1) when X is a bond, n is 1 and $R^3$ is H, or 2) when X is a bond, n is 0 and $R^3$ is a cycloalkyl).

Preferred is aminomethyl-substituted thiazolobenzimidazole derivatives or a salt thereof, in which $R^1$ in the general formula (I) is an oxygen-containing saturated hetero ring- which may be substituted, and $R^3$ is a lower alkyl or a saturated hetero ring-;

more preferred is N-methyl-N-neopentyl-6-[(oxetan-3-ylamino)methyl]thiazolo[3,2-a]benzimidazole-2-carboxamide; 6-{[(1,3-dioxolan-2-ylmethyl)amino]methyl}-N-methyl-N-neopentylthiazolo[3,2-a]benzimidazole-2-carboxamide; or N-neopentyl-6-({[tetrahydro-2H-pyran-4-yl)methyl]amino)methyl)thiazolo[3,2-a]benzimidazole-2-carboxamide or a salt thereof.

The present invention further relates to a medicament which comprises the aforementioned aminomethyl-substituted thiazolobenzimidazole derivative represented by general formula (I) or a salt thereof as the active ingredient, preferably a mGluR 1 receptor antagonist.

More preferably, it is a pharmaceutical composition having a mGluR 1 receptor antagonism, which comprises a mGluR 1 receptor binding-inhibitory amount of the aforementioned aminomethyl-substituted thiazolobenzimidazole derivative or a salt thereof.

Further preferably, it relates to a therapeutic agent for a disease in which activation of mGluR 1 receptor is concerned, which comprises the aforementioned aminomethyl-substituted thiazolobenzimidazole derivative or a salt thereof as the active ingredient, illustratively a therapeutic agent for a neuropathic pain.

Best Mode for Carrying Out the Invention

The following further describes the compound of the invention.

In the definition of general formulae as used herein, unless otherwise noted, the term "lower" means a straight or branched carbon chain having from 1 to 6 carbon atoms.

The "lower alkyl" is a $C_{1-6}$ alkyl, preferably a straight or branched $C_{1-4}$ alkyl such as methyl, ethyl, propyl, isopropyl, t-butyl or the like, more preferably a $C_{1-3}$ alkyl.

The "lower alkylene" is a $C_{1-6}$ alkylene, preferably straight or branched $C_{1-4}$ alkylene (e.g, methylene, ethylene, methylmethylene, trimethylene, propylene, ethylethylene, tetrabutylene or the like), further preferably a $C_{1-3}$ alkylene.

The "lower alkylene substituted with oxo group" means a group in which an optional carbon atom of a straight or branched $C_{2-6}$ alkylene among the aforementioned lower alkylene groups is substituted with oxo group, and preferred is —$CH_2$—C(O)—, —C(O)—$CH_2$—, —$CH_2$—C(O)—$CH_2$—, —$(CH_2)_2$—C(O)— or —C(O)—$(CH_2)_2$—.

The "lower alkenyl" is a $C_{2-6}$ alkenyl, preferably straight or branched $C_{2-4}$ alkenyl (e.g., vinyl, propenyl, butenyl or the like), more preferably a $C_{2-3}$ alkenyl.

The "lower alkynyl" is a $C_{2-6}$ alkynyl, preferably straight or branched $C_{2-4}$ alkynyl (e.g., acetynyl, propynyl, butynyl or the like), more preferably a $C_{2-3}$ alkynyl.

The "halogen" means a halogen atom, for example, it means fluorine, chlorine, bromine or iodine atom.

The "halogeno-lower alkyl" means a group in which optional one or more hydrogen atoms of the aforementioned lower alkyl are substituted with the aforementioned halogen atoms, and trifluoromethyl is desirable.

The "cycloalkyl" means a 3- to 8-membered cycloalkyl, and preferred is cyclopropyl, cyclopentyl, cyclohexyl, cycloheptyl or the like.

The "saturated hetero ring" means a 3- to 8-membered saturated hetero ring containing from 1 to 4 hetero atoms selected from nitrogen atom, oxygen atom and sulfur atom, and its examples include pyrrolidine, piperidine, piperazine, homopiperazine, imidazolidine, morpholine, thiomorpholino, oxirane, oxetane, thietane, tetrahydrofuran, tetrahydropyran, [1,3]dioxolan, [1,4]dioxane, tetrahydrothiophene, [1,4]dithian, hexahydroazepin, hexahydro-pyrrolo[2,1-c][1,4]oxazine and the like.

Preferred is a 5-membered oxygen-containing saturated hetero ring or sulfur-containing saturated hetero ring.

The "oxygen-containing saturated hetero ring" means a saturated hetero ring necessarily containing oxygen atom as a hetero atom in the ring among the aforementioned hetero rings. That is, it means a 3- to 8-membered saturated hetero ring which may contain 1 or 2 nitrogen atom or sulfur atom, in addition to 1 to 3 oxygen atoms. Preferred is a 4- to 6-membered oxygen-containing saturated hetero ring, and more preferred is oxetane, tetrahydrofuran, 1,3-dioxolan tetrahydropyran, or morpholine.

The "sulfur-containing saturated hetero ring" means a saturated hetero ring necessarily containing sulfur atom as a hetero atom in the ring among the aforementioned hetero rings. That is, it means a 3- to 8-membered saturated hetero ring which may contain 1 or 2 nitrogen atom or oxygen atom, in addition to 1 to 3 sulfur atoms. Preferred is a 4- to 6-membered saturated hetero ring, and more preferred is thietane, 1,3-dithiolan, tetrahydrothiophene, thiazolidine or thiomorpholine.

The oxygen-containing saturated hetero ring which may be substituted, the sulfur-containing saturated hetero ring which may be substituted and the cycloalkyl which may be substituted may have 1 to 3 substituent groups on optional carbon atoms or hetero atoms on the ring.

The substituent group means a usual substituent group of a group to be substituted commonly used in said field, and its most desirable examples include a halogen, cyano, a halogeno-lower alkyl, a lower alkyl, OH, a lower alkyl-O—, oxo, a lower alkyl-C(O)—, carboxyl, a lower alkyl-O—C(O)—, a lower alkyl-O-lower alkyl-, nitro, amino which may be substituted with 1 or 2 lower alkyl groups, and the like.

Preferred are a lower alkyl and a lower alkyl-O—.

Depending on the kind of groups, the compound of the invention exists in optical isomer forms (optically active substances, diastereomers and the like). In addition, compounds having amido bond or double bond are included in the compound of the invention, so that tautomers and geometrical isomers also exist. These isomers in the isolated or mixed form are included in the invention.

The compound of the invention forms a salt with an acid or a base. Examples of the salt with an acid include acid addition salts with in organic acids such as mineral acids (e.g., hydrochloric acid, hydrobromic acid, hydroiodic acid, sulfuric acid, nitric acid, phosphoric acid and the like) or with organic acids (e.g., formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, ethanesulfonic acid, glutamic acid and the like).

Examples of the salt with a base include salts with inorganic bases such as sodium, potassium, magnesium, calcium, aluminum and the like, with organic bases such as methylamine, ethylamine, meglumine, ethanolamine and the like, or with basic amino acids such as lysine, arginine, ornithine and the like, as well as an ammonium salt. In addition, the compound of the invention can form hydrates, solvates such as with ethanol and the like and polymorphism.

In addition, a pharmacologically acceptable prodrug is included in the compound of the invention. Examples of the group which forms the pharmacologically acceptable prodrug of the compound of the invention include the groups described in *Prog. Med.*, 5: 2157-2161 (1985) and the groups described in "Development of Medicaments" vol. 7, Molecular Designing, pp. 163-198, published in 1990 by Hirokawa Shoten. Illustratively, it is a group which can be converted into the primary amine, secondary amine, OH, COOH or the like of the invention by hydrolysis or solvolysis or under a physiological condition, and its examples in the case of a prodrug of OH group include —OCO— (lower alkylene which may be substituted) —COOR (R represents H or a lower alkyl, the same shall apply hereinafter), —OCO— (lower alkenylene which may be substituted) —COOR, —OCO— (aryl which may be substituted), —OCO— (lower alkylene) —O— (lower alkylene) —COOR, —OCO—COR, —OCOO— (a lower alkyl which may have be substituted), —OSO₂— (a lower alkylene which be substituted) —COOR, —O-phthalidyl, 5-methyl-1,3-dioxolen-2-on-4-yl-methyloxy or the like.

Also, it is possible to use the compound of the invention in combination with an analgesic, an antiviral agent, a diabetes treating agent or the like.

Examples of the analgesic include pirin, non-pirin and the like non-steroidal anti-inflammatory drugs (NSAID), central analgesics (pentazocine and the like) and opioid analgesics (morphine and the like).

Examples of the diabetes treating agent include sulfonylurea agents (tolbutamide and the like), α-glucosidase inhibitors (acarbose and the like), thiazolidine-dione agents (triglytazone and the like) and biguanide agents (metformin and the like).

Examples of the antiviral agent include acyclovir, paracyclovir, famciclovir and the like.

In addition to the above, the following can be exemplified as agents which can be jointly used.

Carbamazepine and the like anticonvulsants, imiplamine and the like antidepressants, mexiletine and the like antiarrhythmic drugs, lidocaine and the like local anesthetics, xanthine preparations (caffeine and the like), ergotamine agents and calcium antagonists (romelizin hydrochloride and the like).

Production Methods

In this specification, the signs used in the general production methods, reference examples, examples and tables have the following meanings.

DMF: dimethylformamide, DMSO: dimethyl sulfoxide, THF: tetrahydrofuran

Production Method 1: Reductive Amination

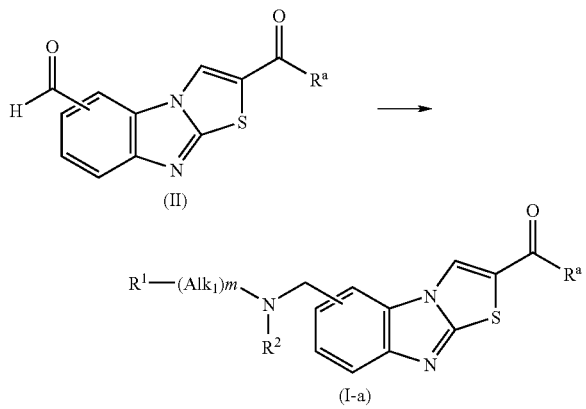

(In the formula, $R^a$ means OH, or a lower alkyl-O—, or $N(R^4)(Alk_2)n-X-R^3$. Other signs are as defined in the foregoing. The same shall apply hereinafter.)

From (II) to (I-a) is a usual reductive amination reaction. That is, the desired (I-a) can be obtained by allowing an aldehyde (II) and a corresponding amine to undergo the reaction using a reducing agent (e.g., sodium triacetoxyborohydride, sodium cyanoborohydride, sodium borohydride or the like) in a solvent (e.g., methylene chloride, 1,2-dichloroethane, chloroform, THF, methanol, ethanol or the like), if necessary in the presence of an acid catalyst (e.g., acetic acid, hydrochloric acid or the like) or Lewis acid (e.g., titanium tetraisopropoxide or the like). The (I-a) can also be synthesized by allowing the (II) and a corresponding amine to undergo the reaction in an inert solvent (e.g., toluene, benzene or the like) at a temperature of from 10° C. to 150° C. under a dehydration reaction condition using a dehydrating agent (e.g., Molecular Sieves or the like) or Dean-Stark filtration equipment for dewatering as occasion demands, thereby forming an imine, and then treating it with a reducing agent (e.g., sodium borohydride or the like) in a solvent (e.g., methanol, ethanol or the like). In addition, the (I-a) can also be synthesized by using a metal catalyst (e.g., palladium or the like) instead of the aforementioned reducing agent under a catalytic reduction condition, illustratively under an atmosphere of hydrogen.

Production Method 2: Alkylation

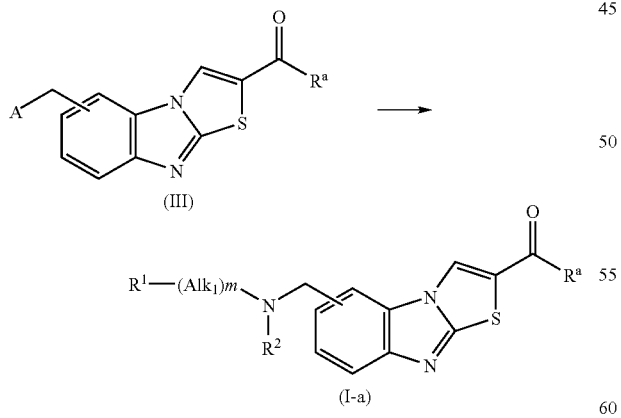

(In the formula, A means a leaving group such as a halogen, sulfonyloxy group or the like.)

From (III) to (I-a) is a usual N-alkylation reaction. That is, the desired (I-a) can be obtained by allowing (III) and a corresponding amine to undergo the reaction at from ice-cooling to 200° C. in an inert solvent (e.g., DMF, acetonitrile, chloroform, THF or the like) in the presence of a base (e.g., potassium carbonate, sodium bicarbonate, triethylamine, ethyl diisopropylamine or the like). The corresponding amine may be used in excess amount in this reaction.

Production Method 3: Amidation

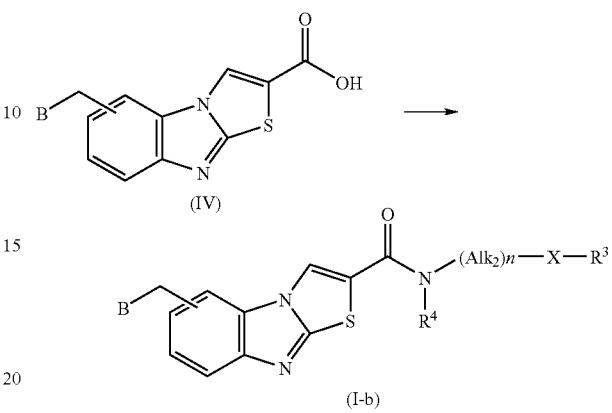

(In the formula, B means OH or $N(R^{2'})(Alk_1)m-R_1$, wherein $R^{2'}$ means H, a lower alkyl which may be substituted, or a general amino group protecting group.)

From (IV) to (I-b) is a usual amidation reaction. That is, the desired (I-b) can be obtained by activating a carboxylic acid (IV) with a condensing agent (e.g., dicyclohexylcarbodiimide, 1-ethyl-3-(3-dimethylaminopropyl)carbodiimide, diphenylphosphoryltriazide, 1,1'-carbonyl-1H-imidazole, 1-hydroxybenzotriazole or the like) in an inert solvent (e.g., DMF, THF, 1,2-dichloroethane, chloroform or the like), and then allowing this active compound to react with a corresponding amine. For activating the carboxylic acid, an acid chloride method in which thionyl chloride, oxalyl chloride or the like is used, a mixed acid anhydride method, or an active phosphoric acid ester method in which phosphorus oxychloride or the like is used can also be used.

Production Method 4: N-Alkylation

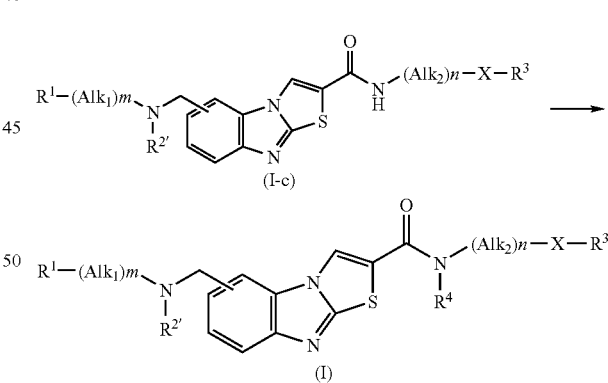

From (I-c) to (I) is a usual N-alkylation reaction. That is, the desired (I) can be obtained by allowing to react with a corresponding alkylating agent (e.g., alkyl halide, sulfonic acid alkyl ester or the like) under from ice-cooling to heating in an inert solvent (e.g., DMF, DMSO, THF, acetone, acetonitrile or the like) using a base (e.g., potassium carbonate, cesium carbonate, sodium hydride, potassium hydroxide or the like).

General protecting groups and the like of hydroxyl group, amino group, ester group and the lie are described in detail in PROTECTIVE GROUPS IN ORGANIC SYNTHESIS, edited by THEODORA W. GREENE and PETER G. M. WUTS, and the disclosure of this reference is incorporated in this specification.

In this connection, the aforementioned production methods are not restricted by the substituent groups of the formulae and can be broadly applied even to a case in which a compound of the invention has similar substituent groups or a case in which a reaction substrate and a reactant have opposite relation.

The compound of the invention produced in this manner is isolated and purified in its free form or as a salt thereof.

The isolation and purification are carried out by employing usual chemical operations such as extraction, concentration, evaporation, crystallization, filtration, recrystallization, various types of chromatography and the like.

Various isomers can be separated by selecting appropriate material compounds or making use of the difference in physiological properties among isomers. For example, optical isomers can be separated into stereochemically pure isomers by selecting an appropriate material or by a method for the optical resolution of racemic compounds (e.g., a method in which they are converted into diastereomer salts with a general optically active base and then subjected to optical resolution).

A pharmaceutical preparation which contains one or more of the compounds of the invention or salts thereof as the active ingredient is prepared using carriers, fillers and other additives generally used in the preparation of medicaments.

The carriers and fillers for pharmaceutical preparation use may be either solid or liquid, and their examples include lactose, magnesium stearate, starch, talc, gelatin, agar, pectin, acacia, olive oil, sesame oil, cacao butter, ethylene glycol and other generally used substances.

It may be administered either by oral administration through tablets, pills, capsules, granules, powders, solutions or the like, or by parenteral administration through injections such as for intravenous injection, intramuscular injection or the like, suppositories, percutaneous preparations and the like. Its dose is optionally decided by taking into consideration conditions of each case such as symptoms, age, sex and the like of the patient to be treated, but, usually, it is orally administered within the range of from 1 to 1,000 mg, preferably from 50 to 200 mg, per day per adult by dividing the daily dose into 1 to several doses per day or intravenously injected within the range of from 1 to 500 mg per day per adult by dividing the daily dose into 1 to several doses per day, or continuously and intravenously injected within the range of from 1 to 24 hours per day. As a matter of course, since the dose varies under various conditions as described in the foregoing, a smaller dose than the above range may be sufficient enough in some cases.

As the solid composition for use in the oral administration according to the invention, tablets, powders, granules and the like are used. In such a solid composition, one or more active substances are mixed with at least one inert diluent such as lactose, mannitol, glucose, hydroxypropylcellulose, microcrystalline cellulose, starch, polyvinyl pyrrolidone or aluminum magnesium metasilicate. In accordance with the usual way, the composition may contain other additives than the inert diluent, which include a lubricant such as magnesium stearate, a disintegrating agent such as starch or calcium cellulose glycolate, a stabilizing agent such as lactose and a solubilization assisting agent such as glutamic acid or aspartic acid. As occasion demands, tablets or pills may be coated with a film of a gastric or enteric substance such as sucrose, gelatin, hydroxypropylcellulose, hydroxypropylmethylcellulose phthalate or the like.

The liquid composition for oral administration use includes pharmaceutically acceptable emulsions, solutions, suspensions, syrups, elixirs and the like and contains a generally used inert diluent such as purified water or ethanol. In addition to the inert diluent, this composition may also contain auxiliary agents such as a moistening agent and a suspending agent, as well as a sweetener, a flavor, an aromatic and an antiseptic.

The injections for parenteral administration use include aseptic aqueous or non-aqueous solutions, suspensions and emulsions. Examples of the diluent for use in the aqueous solutions and suspensions include distilled water for injection and physiological saline. Examples of the diluent for use in the non-aqueous solutions and suspensions include propylene glycol, polyethylene glycol, plant oils (e.g., olive oil), alcohols (e.g., ethanol) and polysorbate 80. Such a composition may further contain auxiliary agents such as an antiseptic, a moistening agent, an emulsifying agent, a dispersing agent, a stabilizing agent (e.g., lactose) and a solubilization assisting agent (e.g., glutamic acid or aspartic acid). They are sterilized by, for example, filtration through a bacteria retaining filter, blending of a germicide or irradiation. Alternatively, they may be used by firstly making into sterile solid compositions and dissolving them in sterile water or a sterile solvent for injection prior to their use.

EXAMPLES

Next, the invention is described further in detail based on examples, but the invention is not limited to these examples. In this connection, methods for producing material compounds used in the Examples are described as reference examples. (The abbreviations used in the following are the same as those used in the production methods.)

$^1$H-NMR; $^1$H-Nuclear magnetic resonance spectrum (This was measured at 300 MHz or 400 MHz, using DMSO-$d_6$ or deuterium chloroform (to be referred to as $CDCl_3$ hereinafter) as the measuring solvent and tetramethylsilane as the internal standard, and the chemical shift was shown by ppm. br; broad, s; singlet, d; doublet, t; triplet, q; quartet, m; multiplet)

MS; Mass spectrometry (FAB+: cation fast atom bombardment mass spectrometry, M: molecular weight)

Ex; Example number

Salt; Salt

Data; Physicochemical properties (mass spectrometry)

Silica gel was used as the filler in the column chromatography used in the purification.

Reference Example 1

6-Hydroxymethyl-N-methyl-N-neopentylthiazolo[3,2-a]benzimidazole-2-carboxamide

In an ice bath, 1-hydroxybenzotriazole (2.03 g) and 1-(3-dimethylaminopropyl)-3-ethylcarbodiimide hydrochloride (5.75 g) were added to a DMF (25 ml) suspension of 6-hydroxymethylthiazolo[3,2-a]benzimidazole-2-carboxylic acid (2.48 g), and the reaction mixture was stirred for 30 minutes in the ice bath and then for 2 hours by removing the ice bath. Methylneopentylamine hydrochloride (2.75 g) and triethylamine (2.8 ml) were added to the reaction mixture, and the resulting reaction mixture was stirred at the same temperature for 2 hours. After completion of the reaction, the reaction mixture was poured into 1 M sodium hydroxide aqueous solution (50 ml). The insoluble matter was collected by filtration, washed with water (150 ml) and then dried by heating under a reduced pressure to obtain the pale yellow title compound (1.98 g).

$^1$H-NMR (DMSO-$d_6$); 0.96 (s, 9H), 3.41 (br, 2H), 3.46 (br, 3H), 4.67 (d, 2H), 5.33 (t, 1H), 7.31 (d, 1H), 7.62 (d, 2H), 8.10 (s, 1H), 9.09 (s, 1H)

Reference Example 2

6-Formyl-N-methyl-N-neopentylthiazolo[3,2-a]benzimidazole-2-carboxamide

Triethylamine (5.58 ml) and sulfur trioxide-pyridine mixture (7.96 g) were added to a DMSO (50 ml) solution of the compound of Reference Example 1 (3.31 g). The reaction mixture was stirred for 6 hours accompanied by exothermic reaction. After completion of the reaction, the reaction mixture was carefully added to sodium bicarbonate aqueous solution. The insoluble matter was collected by filtration, washed with water (500 ml) and then dried by heating under a reduced pressure to obtain the pale ivory-colored title compound (3.21 g).

$^1$H-NMR (DMSO-d$_6$); 0.97 (s, 9H), 3.42 (br, 2H), 3.48 (br, 3H), 7.85 (d, 1H), 7.95 (dd, 1H), 8.69 (d, 1H), 9.22 (s, 1H), 10.09 (s, 1H)

Reference Example 3

6-Chloromethyl-N-methyl-N-neopentylthiazolo[3,2-a]benzimidazole-2-carboxamide Hydrochloride DMF (one drop) was added to a thionyl chloride (5 ml) solution of the compound of Reference Example 1 (994 mg). The reaction mixture was stirred for 30 minutes accompanied by exothermic reaction and foaming. After completion of the reaction, the reaction mixture was diluted with toluene (40 ml). The precipitate was collected by filtration, washed with toluene and then dried by heating under a reduced pressure to obtain the title compound (1,105 mg).

$^1$H-NMR (DMSO-d$_6$); 0.97 (s, 9H), 3.42 (br, 2H), 3.48 (br, 3H), 4.98 (s, 2H), 7.51(d, 1H), 7.74 (d, 1H), 8.27 (s, 1H), 9.20 (s, 1H)

Reference Example 4

Ethyl 6-formylthiazolo[3,2-a]benzimidazole-2-carboxylate

Triethylamine (39.02 ml) and sulfur trioxide-pyridine mixture (55.71 g) were added to a DMSO (300 ml) solution of ethyl 6-hydroxymethylthiazolo[3,2-a]benzimidazole-2-carboxylate (19.34 g). The reaction mixture was stirred for 2 hours accompanied by exothermic reaction. After completion of the reaction, the reaction mixture was carefully added to saturated sodium bicarbonate aqueous solution. The insoluble matter was collected by filtration, washed with water and then dried by heating under a reduced pressure to obtain the pale ivory-colored title compound (19.10 g).

$^1$H-NMR (DMSO-d$_6$); 1.36 (t, 3H), 4.39 (q, 2H), 7.87 (d, 1H), 7.97 (dd, 1H), 8.76 (d, 1H), 9.51 (s, 1H), 10.08 (s, 1H)

Reference Example 5

Ethyl 6-({[((R)-tetrahydro-2-furyl)methyl]amino}methyl)thiazolo[3,2-a]benzimidazole-2-carboxylate (R)-Tetrahydrofurfurylamine (3.1 ml) was added to a dichloroethane (200 ml) solution of the compound of Reference Example 4 (5.49 g), and stirred at room temperature for 1 hour. Sodium triacetoxyborohydride (8.48 g) was added to the reaction mixture and stirred at the room temperature for a whole day and night. After completion of the reaction, the reaction mixture was mixed with saturated sodium bicarbonate aqueous solution and extracted with chloroform. The organic layer was collected, washed with saturated sodium bicarbonate aqueous solution, water and saturated brine and then dried with anhydrous magnesium sulfate and concentrated under a reduced pressure. The residue was purified by a column chromatography (eluent; ethyl acetate, then ethyl acetate methanol=95:5 and further chloroform:methanol=10:1) to obtain the title compound (6.10 g).

$^1$H-NMR (CDCl$_3$); 1.42 (t, 3H), 1.52-1.61 (m, 1H), 1.85-2.02 (m, 3H), 2.68 (dd, 1H), 2.75 (dd, 1H), 3.72-3.79 (m, 1H), 3.82-3.88 (m, 1H), 4.00 (s, 2H), 4.02-4.09 (m, 1H), 4.42 (q, 2H), 7.37 (dd, 1H), 7.72 (d, 1H), 7.75 (d, 1H), 8.41 (s, 1H)

Reference Example 6

Ethyl 6-({tert-butoxycarbonyl-[((R)-tetrahydro-2-furyl)methyl]amino}methyl)thiazolo[3,2-a]benzimidazole-2-carboxylate A chloroform (30 ml) solution of di-tert-butyl dicarbonate (3.71 g) was added to a chloroform (60 ml) solution of the compound of Reference Example 5 (6.10 g) and stirred at room temperature for 2 hours. After completion of the reaction, the reaction mixture was concentrated under a reduced pressure to obtain the light brown title compound (7.74 g).

$^1$H-NMR (CDCl$_3$); 1.43 (t, 3H), 1.36-1.57 (m, 9H), 1.81-2.02 (m, 3H), 3.02-3.22 (m, 1H), 3.28-3.65 (m, 1H), 3.73-3.80 (m, 1H), 3.81-3.91 (m, 1H), 4.01-4.18 (m, 1H), 4.43 (t, 2H), 4.64 (d, 1H), 4.84 (d. 1H), 7.33 (br, 1H), 7.61 (br, 1H), 7.73 (d, 1H), 8.41 (s, 1H)

Reference Example 7

6-({tert-butoxycarbonyl-[((R)-tetrahydro-2-furyl)methyl]amino}methyl)thiazolo[3,2-a]benzimidazole-2-carboxylic acid A methanol (100 ml) suspension of the compound of Reference Example 6 (7.74 g) was mixed with 1 M sodium hydroxide aqueous solution (40 ml) and stirred at room temperature for 2 hours. After completion of the reaction, the reaction mixture was mixed with 1 M hydrochloric acid aqueous solution (40 ml). The precipitate was collected by filtration, washed with water and then dried by heating under a reduced pressure to obtain the colorless title compound (6.57 g).

$^1$H-NMR (DMSO-d$_6$); 1.37 (br, 3H), 1.45 (br, 6H), 1.73-1.93 (m, 3H), 3.06-3.48 (m, 3H), 3.65 (dd, 1H), 3.77 (dd, 1H), 3.98-4.07 (m, 1H), 4.55 (d, 1H), 4.69 (d, 1H), 7.27 (dd, 1H), 7.67 (d, 1H), 8.01 (d, 1H), 9.31 (s, 1H), 13.84 (br, 1H)

Reference Example 8

6-Hydroxymethyl-N-neopentylthiazolo[3,2-a]benzimidazole-2-carboxamide

1-Hydroxybenzotriazole (10.1 g) and 1-(3-dimethylaminopropyl)-3-ethylcarbodiimide hydrochloride (28.8 g) were added to a DMF (500 ml) suspension of 6-hydroxymethylthiazolo[3,2-a]benzimidazole-2-carboxylic acid (12.4 g), and the reaction mixture was stirred at room temperature for 2 hours. Neopentylamine (17.7 ml) was added to the reaction mixture, and the resulting reaction mixture was stirred at the same temperature for 2 hours. After completion of the reaction, the reaction mixture was poured into 0.5 M sodium hydroxide aqueous solution (2 l). The insoluble matter was collected by filtration, washed with water and then with a mixed solvent of hexane and diethyl ether (mixing ratio; 3:1) and then dried by heating under a reduced pressure to obtain the title compound (12.0 g).

$^1$H-NMR (DMSO-$d_6$); 0.94 (s, 9H), 3.13 (d, 2H), 4.68 (d, 2H), 5.33 (t, 1H), 7.33 (d, 1H), 7.65 (d, 2H), 7.88 (br, 1H), 8.52 (t, 1H), 9.14 (s, 1H)

Reference Example 9

6-Formyl-N-neopentylthiazolo[3,2-a]benzimidazole-2-carboxamide

Triethylamine (21.1 ml) was added to a DMSO (200 ml) solution of the compound of Reference Example 8 (12.0 g), and then a sulfur trioxide-pyridine mixture (30.0 g) was gradually added thereto at room temperature. After completion of the addition, the reaction mixture was stirred at room temperature for 1.5 hours. After completion of the reaction, the reaction mixture was added to 0.1 M sodium hydroxide aqueous solution (2 l). The precipitate was collected by filtration, washed with water and diethyl ether in that order and then dried by heating under a reduced pressure to obtain the title compound (10.3 g).

$^1$H-NMR (DMSO-$d_6$); 0.94 (s, 9H), 3.14 (d, 2H), 7.87 (d, 1H), 7.96 (d, 2H), 8.52 (br, 1H), 8.67 (t, 1H), 9.25 (s, 1H), 10.11 (s, 1H)

Reference Example 10

N-(1,3-Dioxolan-2-ylmethyl)-6-hydroxymethyl-N-methylthiazolo[3,2-a]benzimidazole-2-carboxamide 1-Hydroxybenzotriazole (10.1 g) and 1-(3-dimethylaminopropyl)-3-ethylcarbodiimide hydrochloride (28.8 g) were added to a DMF (500 ml) suspension of 6-hydroxymethylthiazolo[3,2-a]benzimidazole-2-carboxylic acid (12.4 g), and the reaction mixture was stirred at room temperature for 1.5 hours. N-(1,3-Dioxolan-2-ylmethyl)-N-methylamine (17.1 ml) was added to the reaction mixture, and the resulting reaction mixture was stirred at the same temperature for 1 hour. After completion of the reaction, the reaction mixture was poured into 0.5 M sodium hydroxide aqueous solution (2 l). The insoluble matter was collected by filtration, washed with water and then with a mixed solvent of hexane and diethyl ether (mixing ratio; 3:1) and then dried by heating under a reduced pressure to obtain the title compound (8.62 g).

$^1$H-NMR (DMSO-$d_6$); 3.07-3.98 (m, 9H), 4.67 (d, 2H), 5.08 (br, 1H), 5.32 (t, 1H), 7.31 (d, 1H), 7.62 (d, 1H), 8.09 (br, 1H), 9.04 (br, 1H)

Reference Example 11

N-(1,3-Dioxolan-2-ylmethyl)-6-formyl-N-methylthiazolo[3,2-a]benzimidazole-2-carboxamide Triethylamine (13.8 ml) was added to a DMSO (180 ml) solution of the compound of Reference Example 10 (8.6 g), and then a sulfur trioxide-pyridine mixture (19.7 g) was gradually added thereto at room temperature. After completion of the addition, the reaction mixture was stirred at room temperature for 1.5 hours. After completion of the reaction, the reaction mixture was added to 0.07 M sodium hydroxide aqueous solution (2.15 l). The precipitate was collected by filtration, washed with water and diethyl ether in that order and then dried by heating under a reduced pressure to obtain the title compound (4.41 g).

$^1$H-NMR (DMSO-$d_6$); 3.30-3.98 (m, 9H), 5.09 (br, 1H), 7.86 (d, 1H), 7.96 (d, 1H), 8.71 (br, 1H), 9.20 (br, 1H), 10.01 (s, 1H)

Reference Example 12

(4-Methoxytetrahydropyran-4-yl)methylamine

Under ice-cooling, a diethyl ether (5 ml) solution of 4-cyano-4-methoxytetrahydropyran (600 mg; *Chemistry Letters*, pp. 937-940, 1984) was added dropwise to a diethyl ether (10 ml) suspension of lithium aluminum hydride (242 mg) spending 20 minutes and, after completion of the dropwise addition, stirred at room temperature for 4 hours. After completion of the reaction, the reaction mixture was ice-cooled, and sodium sulfate decahydrate was gradually added to the reaction mixture until foaming stopped. After completion of the addition, the insoluble matter was filtered, and the filtered solid was washed with diethyl ether. The filtrate and washed solution were combined and concentrated under a reduced pressure to obtain the title compound (597 mg).

$^1$H-NMR (DMSO-$d_6$); 1.17 (br, 2H), 1.40-1.47 (m, 2H), 1.57-1.62 (m, 2H), 2.53 (br, 2H), 3.07 (s, 3H), 3.47-3.66 (m, 4H)

Reference Example 13

2-(tert-Butoxycarbonyl)aminomethyl-1,3-dithiolan

At room temperature, di-tert-butyl dicarbonate (1.69 g) was added to an ethyl acetate (15 ml) solution of 1,3-dithiolan-2-ylmethylamine (1.0 g) and stirred at room temperature for a whole day and night. After completion of the reaction, the reaction mixture was separated using a mixed solution of ethyl acetate and water. The organic layer was washed with water and saturated brine, dried with anhydrous sodium sulfate and then concentrated under a reduced pressure to obtain the title compound (1.85 g).

$^1$H-NMR (DMSO-$d_6$); 1.38 (s, 9H), 3.10 (t, 2H), 3.18 (br, 4H), 4.49 (t, 1H), 7.11 (br, 1H)

Reference Example 14

2-Methylaminomethyl-1,3-dithiolan

Under ice-cooling, a tetrahydrofuran (20 ml) solution of the compound of Reference Example 13 (1.85 g) was added dropwise to a tetrahydrofuran (20 ml) suspension of lithium aluminum hydride (597 mg) spending 20 minutes and, after completion of the dropwise addition, heated under reflux for a whole day and night. After completion of the reaction, the reaction mixture was ice-cooled, and sodium sulfate decahydrate was gradually added to the reaction mixture until foaming stopped. After completion of the addition, the insoluble matter was filtered, and the filtered solid was washed with diethyl ether. The filtrate and washed solution were combined, concentrated under a reduced pressure and then dried by heating under a reduced pressure to obtain the title compound (782 mg).

$^1$H-NMR (DMSO-$d_6$); 1.75 (br, 1H), 2.28 (d, 3H), 2.67 (dd, 2H), 3.14-3.19 (m, 4H), 4.55 (t, 1H)

Reference Example 15

N-Methyl-6-[(2-morpholin-4-ylethoxy)methyl]-N-neopentylthiazolo[3,2-a]benzimidazole-2-carboxamide dihydrochloride In an ice bath, sodium hydride (68 mg) was added to a DMF (10 ml) suspension of the compound of Reference Example 3 (566 mg) and stirred in the ice bath for 5 minutes (reaction mixture 1). Also, in an ice bath, sodium hydride (68 mg) was added to a DMF (10 ml) solution of 2-morpholin-4-ylethanol (0.178 ml) and stirred in the ice bath for 35 minutes (reaction mixture 2). In an ice bath, the reaction mixture 2 was added dropwise to the reaction mixture 1 and, after warming up to room temperature, sodium hydride (51 mg) was gradually added thereto and stirred at room temperature for a whole day and night. After completion of the reaction, the reaction mixture was poured into saturated sodium bicarbonate aqueous solution and extracted with ethyl acetate. The organic layer was washed with water and saturated brine, dried with anhydrous sodium sulfate and then concentrated under a reduced pressure. The resulting residue was purified by a column chromatography (eluent; chloroform, then chloroform methanol=90:10 and then chloroform:methanol=85:15). The formed product was made into hydrochloride in the usual way, and the thus crystallized residue was recrystallized from ethanol and ethyl acetate to obtain the title compound (92 mg).

$^1$H-NMR (DMSO-$d_6$); 0.97 (s, 9H), 3.09-3.18 (m, 2H), 3.38-3.49 (m, 9H), 3.85-3.96 (m, 6H), 4.72 (s, 2H), 7.41 (dd, 1H), 7.72 (d, 1H), 8.35 (br, 1H), 9.27(s, 1H), 11.19 (br, 1H)

Example 5

N-Methyl-6-methoxybutylaminomethyl-N-neopentylthiazolo[3,2-a]benzimidazole-2-carboxamide dihydrochloride A THF (10 ml) solution of the compound of Example 4 (304 mg) was mixed with di-tert-butyl dicarbonate (166 mg) and stirred at room temperature for 1 hour. After completion of the reaction, the reaction mixture was concentrated under a reduced pressure, and the thus obtained residue was purified by a column chromatography (eluent; hexane:ethyl acetate=50:50-0:100) to obtain N-methyl-6-[(N-tert-butoxycarbonyl)-4-hydroxybutyl]aminomethyl-N-neopentylthiazolo[3,2-a]benzimidazole-2-carboxamide (380 mg). In an ice bath, methyl iodide (71 μl) and sodium hydride (36 mg) were added to a DMF (5 ml) solution of this compound (380 mg) and stirred in the ice bath for 1 hour. Methyl iodide (213 μl) was further added to the reaction mixture and stirred at room temperature for a whole day and night. After completion of the reaction, the reaction mixture was mixed with saturated sodium bicarbonate aqueous solution and extracted with ethyl acetate. The organic layer was collected, washed with water and saturated brine, dried with anhydrous magnesium sulfate and then concentrated under a reduced pressure. The thus obtained residue was purified by a column chromatography (eluent; hexane:ethyl acetate=70:30-10:90) to obtain N-methyl-6-[(N-tert-butoxycarbonyl)-6-methoxybutyl]aminomethyl-N-neopentylthiazolo[3,2-a]benzimidazole-2-carboxamide (50 mg). In an ice bath, 4 M hydrochloric acid-ethyl acetate solution (6 ml) was added to an ethyl acetate (2 ml) solution of this compound (50 mg) and then stirred for 1 hour by removing the ice bath. After completion of the reaction, the reaction mixture was dissolved in ethanol and then concentrated under a reduced pressure. The resulting residue was washed with a mixed solvent of hot ethanol-ethyl acetate to obtain the title compound (40 mg).

$^1$H-NMR (DMSO-$d_6$); 0.97 (s, 1H), 1.50-1.58 (m, 2H), 1.67-1.77 (m, 2H), 2.91 (br, 2H), 3.31 (t, 1H), 3.42 (br, 2H), 3.48 (br, 3H), 4.22-4.28 (m, 2H), 6.52 (br, 2H), 7.69 (dd, 1H), 7.79 (d, 1H), 8.25 (s, 1H), 9.16 (s, 1H), 9.44 (br, 2H)

MS (FAB+); 417 (M+1)

Example 6

N-Methyl-N-neopentyl-6-[(oxetan-3-ylamino)methyl]thiazolo[3,2-a]benzimidazole-2-carboxamide 1.5 Fumarate A DMF (40 ml) solution of the compound of Reference Example 3 (386 mg) was mixed with oxetan-3-ylamine hydrochloride (548 mg), potassium carbonate (691 mg) and triethylamine (0.67 ml), and the mixture was stirred in an oil bath of 50° C. for a whole day and night. After completion of the reaction, the reaction mixture was poured into a mixed solution of ethyl acetate and water. The insoluble matter was filtered, and the resulting water layer was extracted with ethyl acetate. The organic layer was collected, washed with water and saturated brine, dried with anhydrous magnesium sulfate and then concentrated under a reduced pressure. The thus obtained residue was purified by a fractional thin layer chromatography (eluent; chloroform:methanol=9:1). The thus formed product was made into fumarate in the usual way and recrystallized from ethanol and ethyl acetate to obtain the title compound (65 mg).

$^1$H-NMR (DMSO-$d_6$); 0.97 (s, 9H), 3.42 (br, 2H), 3.47 (br, 3H), 3.84 (s, 2H), 3.93-4.01 (m, 1H), 4.35 (t, 2H), 4.59 (t, 2H), 6.62 (s, 3H), 7.34 (dd, 1H), 7.62 (d, 1H), 8.07 (br, 1H), 9.06 (s, 1H)

MS (FAB+); 387 (M+1)

The compounds of Examples 8, 9, 16 and 19 were synthesized by the same method of Example 6.

Example 6 (Another Method)

N-Methyl-N-neopentyl-6-[(oxetan-3-ylamino)methyl]thiazolo[3,2-a]benzimidazole-2-carboxamide 1.5 Fumarate A dichloroethane (10 ml) solution of the compound of Reference Example 2 (329 mg) was mixed with oxetan-3-ylamine hydrochloride (329 mg), triethylamine (418 μl) and acetic acid (171 μl), and the mixture was stirred at room temperature for 2 hours. The reaction mixture was mixed with sodium triacetoxyborohydride (1,060 mg) and further stirred at room temperature for 22 hours. After completion of the reaction, the reaction mixture was mixed with water and 1 M sodium hydroxide aqueous solution and extracted with 5% methanol-containing chloroform. The organic layer was collected, washed with saturated brine, dried with anhydrous magnesium sulfate and then concentrated under a reduced pressure. The resulting residue was purified by a column chromatography (eluent; chloroform:methanol=100:0-100:10) to obtain N-methyl-N-neopentyl-6-[(oxetan-3-ylamino)methyl]thiazolo[3,2-a]benzimidazole-2-carboxamide (343 mg). The thus obtained compound was dissolved in ethanol and mixed with fumaric acid (165 mg), and then the mixture was concentrated under a reduced pressure. By recrystallizing the thus obtained residue from ethanol and ethyl acetate, the title compound (298 mg) was obtained.

Example 7

N-Methyl-6-({[(3-methyloxetan-3-yl)methyl]amino}methyl)-N-neopentylthiazolo[3,2-a]benzimidazole-2-carboxamide A DMF (10 ml) solution of the compound of Reference Example 3 (1.62 g) was mixed with potassium phthalimide (2.31 g) and potassium carbonate (2.87), and the mixture was stirred at room temperature for 14 hours. After completion of the reaction, the reaction mixture was poured into water (100 ml) and stirred at room temperature for 30 minutes. The precipitate was collected by filtration, washed with water and then with a mixed solvent of hexane and diethyl ether (mixing ratio; 3:1) and dried by heating under a reduced pressure to obtain N-methyl-N-neopentyl-6-[(phthalimide)methyl]thiazolo[3,2-a]benzimidazole-2-carboxamide (1.76 g). Under ice-cooling, 40% methylamine-methanol solution (2.4 ml) was added dropwise to a methanol (20 ml) solution of this compound (1.75 g) and, after completion of the dropwise addition, this was heated under reflux for 1 hour. After completion of the reaction, the reaction mixture was concentrated under a reduced pressure, and the resulting residue was purified by a column chromatography (eluent; chloroform:methanol: 29% aqueous ammonia=100:0:0-93:7:0.7-90:10:1) to obtain 6-aminomethyl-N-methyl-N-neopentylthiazolo[3,2-a]benzimidazole-2-carboxamide (702 mg). A methanol (30 ml) solution of this compound (524 mg) was mixed with (3-methyloxetan-3-yl)methyl methanesulfonate (286 mg) and sodium carbonate (496 mg) and stirred in an oil bath of 100° C. for 6 days. After completion of the reaction, the reaction mixture was mixed with water and extracted with ethyl acetate. The organic layer was washed with water and saturated brine, dried with anhydrous sodium sulfate and then concentrated under a reduced pressure. By recrystallizing the resulting residue from hexane and ethyl acetate, the title compound (316 mg) was obtained.

$^1$H-NMR (DMSO-$d_6$); 0.96 (s, 9H), 1.25 (s, 3H), 2.27 (br, 1H), 2.67 (br, 2H), 3.41 (br, 2H), 3.47 (br, 3H), 3.88 (br, 2H), 4.17 (d, 2H), 4.34 (d, 2H), 7.39 (dd, 1H) 7.63 (d, 1H), 8.05 (s, 1H), 9.05 (s, 1H)

MS (FAB+); 415 (M+1)

Example 10

N-Methyl-N-neopentyl-6-({[((R)-tetrahydro-2-furfuryl)methyl]amino}methyl)thiazolo[3,2-a]benzimidazole-2-carboxamide dihydrochloride A DMF (5 ml) solution of the compound of Reference Example 3 (386 mg) was mixed with potassium carbonate (691 mg) and (R)-tetrahydrofurfurylamine (506 mg), and the mixture was stirred at room temperature for 3 hours. After completion of the reaction, the reaction mixture was poured into a mixed solution of ethyl acetate and water. The insoluble matter was filtered and the water layer was extracted with ethyl acetate. The organic layers were collected, washed with water and saturated brine, dried with anhydrous magnesium sulfate and then concentrated under a reduced pressure. The resulting residue was purified by a column chromatography (eluent; ethyl acetate and then chloroform:methanol=10:1). The thus formed product was made into hydrochloride in the usual way and then recrystallized from ethanol and ethyl acetate to obtain the title compound (192 mg).

$^1$H-NMR (DMSO-$d_6$); 0.97 (s, 9H), 1.52-1.62 (m, 1H), 1.77-1.89 (m, 2H), 1.95-2.05 (m, 1H), 2.80-2.92 (m, 1H), 2.98-3.08 (m, 1H), 3.42 (br, 2H), 3.48 (br, 3H), 3.71 (dd, 1H), 3.80 (dd, 1H), 4.17-4.36 (m, 3H), 7.69 (d, 1H), 7.79 (d, 1H), 8.27 (s, 1H), 9.18 (s, 1H), 9.34 (br, 1H), 9.68 (br, 1H)

MS (FAB+); 415 (M+1)

Example 11

N-Methyl-N-neopentyl-6-({[((S)-tetrahydro-2-furfuryl)methyl]amino}methyl)thiazolo[3,2-a]benzimidazole-2-carboxamide Dihydrochloride A DMF (12 ml) solution of the compound of Reference Example 3 (340 mg) was mixed with (S)-tetrahydrofurfurylamine (492 mg) and potassium carbonate (672 mg), and the mixture was stirred in an oil bath of 50° C. for 13 hours. After completion of the reaction, the reaction mixture was mixed with water and extracted with ethyl acetate. The insoluble matter was filtered, and the water layer was extracted with ethyl acetate. The organic layers were washed with water and then extracted with 1 M hydrochloric acid aqueous solution. The water layer was washed with chloroform, and then the water layer was adjusted to basic (pH 9-11) with saturated sodium bicarbonate aqueous solution and extracted with chloroform. The organic layer was dried with anhydrous sodium sulfate and concentrated under a reduced pressure. The product was made into hydrochloride in the usual way and recrystallized from 2-propanol to obtain the title compound (165 mg).

$^1$H-NMR (DMSO-$d_6$); 0.97 (s, 9H), 1.51-1.60(m, 1H), 1.79-1.86 (m, 2H), 1.96-2.04 (m, 1H), 2.86-2.91 (m, 1H), 3.04-3.07 (m, 1H), 3.42 (br, 2H), 3.47 (br, 3H), 3.72 (dd, 1H), 3.80 (dd, 1H), 4.19-4.31 (m, 3H), 7.62 (d, 1H), 7.78 (d, 1H), 8.20 (s, 1H), 9.10 (s, 1H), 9.20-9.46 (m, 2H)

MS (FAB+); 415 (M+1)

Example 12

6-{[(1,3-Dioxolan-2-ylmethyl)amino]methyl}-N-methyl-N-neopentylthiazolo[3,2-a]benzimidazole-2-carboxamide dihydrochloride A DMF (12 ml) solution of the compound of Reference Example 3 (340 mg) was mixed with 1,3-dioxolan-2-ylmethylamine (167 mg) and potassium carbonate (672 mg), and the mixture was stirred in an oil bath of 50° C. for 12.5 hours. After completion of the reaction, the reaction mixture was mixed with water and extracted with ethyl acetate. The insoluble matter was filtered, and the water layer was extracted with ethyl acetate. The organic layer was washed with water and then extracted with 1 M hydrochloric acid aqueous solution. The water layer was washed with chloroform, and then the water layer was adjusted to basic (pH 9-11) with saturated sodium bicarbonate aqueous solution and extracted with chloroform. The organic layer was dried with anhydrous sodium sulfate and then concentrated under a reduced pressure. The resulting product was made into hydrochloride in the usual way and recrystallized from 2-propanol to obtain the title compound (104 mg).

$^1$H-NMR (DMSO-$d_6$); 0.97 (s, 9H), 3.12-3.13 (m, 2H), 3.42 (br, 2H), 3,47 (br, 3H), 3.85-3.93 (m, 2H), 3.96-4.04 (m, 2H), 4.33 (br, 2H), 5.19 (t, 1H), 7.59 (dd, 1H), 7.77 (d, 1H), 8.19 (s, 1H), 9.08 (s, 1H), 9.30 (br, 1H), 9.37 (br, 1H)

MS (FAB+); 417 (M+1)

Example 12 (Another Method)

A dichloroethane (40 ml) solution of the compound of Reference Example 2 (1,364 mg) was mixed with 1,3-dioxolan-2-ylmethylamine (1,281 mg) and acetic acid (711 µl), and the mixture was stirred at room temperature for 2 hours. The reaction mixture was mixed with sodium triacetoxyborohydride (4,387 mg) and further stirred at room temperature for 20 hours. After completion of the reaction, the reaction mixture was mixed with 1 M sodium hydroxide aqueous solution and extracted with 5% methanol-containing chloroform. The organic layer was collected, washed with saturated brine, dried with anhydrous magnesium sulfate and then concentrated under a reduced pressure. The resulting residue was purified by a column chromatography (eluent; chloroform:methanol=95:5) to obtain 6-{[(1,3-Dioxolan-2-ylmethyl)amino]methyl}-N-methyl-N-neopentylthiazolo[3,2-a]benzimidazole-2-carboxamide (1,564 mg). The thus obtained compound was dissolved in ethanol and mixed with 1 M hydrochloric acid aqueous solution, and then the mixture was concentrated under a reduced pressure. By recrystallizing the thus obtained residue from ethanol and ethyl acetate, the title compound (1,410 mg) was obtained.

Example 13

N-Methyl-N-neopentyl-6-({methyl[((R)-tetrahydro-2-furfuryl)methyl]amino}methyl)thiazolo[3,2-a] benzimidazole-2-carboxamide Dihydrochloride Under ice cooling, a DMF (20 ml) solution of the compound of Example 24 (448 mg) was mixed with methyl iodide (146 µl) and sodium hydride (88 mg), and the mixture was stirred under ice-cooling for 2.5 hours. After completion of the reaction, the reaction mixture was poured into saturated sodium bicarbonate aqueous solution and extracted with ethyl acetate. The organic layer was washed with water and saturated brine, dried with anhydrous sodium sulfate and then concentrated under a reduced pressure. The resulting residue was purified by a column chromatography (eluent; chloroform, then chloroform:methanol=90:10 and then chloroform:methanol=85:15). The thus obtained product was made into hydrochloride in the usual way and recrystallized from ethanol and ethyl acetate to obtain the title compound (140 mg).

$^1$H-NMR (DMSO-$d_6$); 0.97 (s, 9H), 1.48-1.55 (m, 1H), 1.79-1.86 (m, 2H), 2.01-2.07 (m, 1H), 2.74-2.75 (m, 3H), 3.03-3.37 (m, 2H), 3.42 (brs, 2H), 3.49 (brs, 3H), 3.71-3.86 (m, 2H), 4.39-4.47 (m, 2H), 4.53-4.63 (m, 1H), 7.72 (ddd, 1H), 7.81 (d, 1H), 8.36 (d, 1H), 9.22 (s, 1H), 10.67 (br, 1H), 11.06 (br, 1H)

MS (FAB+); 429 (M+1)

Example 15

N-Methyl-N-neopentyl-6-{[(tetrahydro-2H-pyran-4-yl)amino]methyl}thiazolo[3,2-a]benzimidazole-2-carboxamide dihydrochloride A DMF (12 ml) solution of the compound of Reference Example 3 (340 mg) was mixed with tetrahydropyran-4-ylamine hydrochloride (367 mg) and potassium carbonate (672 mg), and the mixture was stirred in an oil bath of 50° C. for 36 hours. After completion of the reaction, the reaction mixture was mixed with water and extracted with ethyl acetate. The insoluble matter was filtered, and the water layer was extracted with ethyl acetate. The organic layer was washed with water and then extracted with 1 M hydrochloric acid aqueous solution. The water layer was washed with chloroform, and then the water layer was adjusted to basic (pH 9-11) with saturated sodium bicarbonate aqueous solution and extracted with chloroform. The organic layer was dried with anhydrous sodium sulfate and then concentrated under a reduced pressure. The resulting product was made into hydrochloride in the usual way and recrystallized from ethanol to obtain the title compound (77 mg).

$^1$H-NMR (DMSO-$d_6$); 0.97 (s, 9H), 1.71 (ddd, 2H), 2.06-2.12 (m, 2H), 3.27-3.38 (m, 3H), 3.43 (br, 2H), 3.47 (br, 3H), 3.94 (dd, 2H), 4.28-4.32 (m, 2H), 7.66 (d, 1H), 7.79 (d, 1H), 8.24 (s, 1H), 9.11 (s, 1H), 9.32-9.54 (m, 2H)

MS (FAB+); 415 (M+1)

Example 17

N-Methyl-N-neopentyl-6-({[(tetrahydro-2H-pyran-4-yl)methyl]amino}methyl)thiazolo[3,2-a]benzimidazole-2-carboxamide dihydrochloride A dichloroethane (10 ml) solution of the compound of Reference Example 2 (230 mg) was mixed with acetic acid (208 µl) and (tetrahydropyran-4-yl)methylamine (252 mg), and the mixture was stirred at room temperature for 1.5 hours. The reaction mixture was mixed with sodium triacetoxyborohydride (278 mg) and further stirred at room temperature for 1.5 hours. After completion of the reaction, the reaction solution was adjusted to acidic (pH 1-3) by adding 1 M hydrochloric acid aqueous solution (30 ml) and then extracted with 1 M hydrochloric acid aqueous solution and washed with chloroform. The water layer was adjusted to basic (pH 11-13) by adding 3 M sodium hydroxide aqueous solution (30 ml) and then extracted with chloroform. The organic layer was dried with anhydrous sodium sulfate and concentrated under a reduced pressure. The resulting residue was purified by a column chromatography (eluent; chloroform:methanol: 29% aqueous ammonia=100:0:0-93:7:0.7-90:10:1). By making the product into hydrochloride in the usual way and recrystallizing it from ethanol and ethyl acetate, the title compound (220 mg) was obtained.

$^1$H-NMR (DMSO-$d_6$); 0.97 (s, 9H), 1.14-1.26 (m, 2H), 1.67-1.75 (m, 2H), 1.97-2.10 (m, 1H), 2.76-2.83 (m, 2H), 3.26 (dt, 2H), 3.42 (br, 2H), 3.48 (br, 3H), 3.83 (dd, 2H), 4.23-4.32 (m, 2H), 7.76 (d, 1H), 7.80 (d, 1H), 8.31 (s, 1H), 9.21 (s, 1H), 9.48-9.70 (m, 2H)

MS (FAB+); 429 (M+1)

The compounds of Examples 14 and 18 were synthesized by the same method of Example 17.

Example 23

(R)-N-Neopentyl-6-{[(tetrahydro-3-furyl)amino]methyl}thiazolo[3,2-a]benzimidazole-2-carboxamide dihydrochloride A dichloroethane (15 ml) solution of the compound of Reference Example 9 (400 mg) was mixed with acetic acid (362 µl), (R)-(tetrahydrofuran-3-yl)amine p-toluenesulfonate (988 mg) and triethylamine (530 µl), and the mixture was stirred at room temperature for 1 hour. Subsequently, this was mixed with sodium triacetoxyborohydride (485 mg) and further stirred at room temperature for 2 hours. After completion of the reaction, the reaction mixture was mixed with saturated sodium bicarbonate aqueous solution and stirred, and then the insoluble matter was filtered and washed with chloroform. The filtrate and washing solution were combined and concentrated under a reduced pressure, and the resulting residue was purified by a column chromatography (eluent; chloroform:methanol: 29% aqueous ammonia=100:0:0-93:7:0.7-90:10:1). The thus obtained product was extracted with chloroform, washed with 1 M sodium hydroxide aqueous solution and saturated brine, and then the organic layer was dried with anhydrous sodium sulfate and concentrated under a reduced pressure. By making the product into hydrochloride in the usual way and washing it with a mixed solvent of ethanol and ethyl acetate, the title compound (346 mg) was obtained.

$^1$H-NMR (DMSO-d$_6$); 0.92 (s, 9H), 2.09-2.25 (m, 2H), 3.12 (d, 2H), 3.66 (dd, 1H), 3.74-3.85 (m, 2H), 3.81-3.98 (m, 2H), 4.25-4.40 (m, 2H), 7.68 (d, 1H), 7.78 (d, 1H), 8.20 (s, 1H), 9.08 (t, 1H), 9.44 (s, 1H), 9.92 (br, 2H)

MS (FAB+); 387 (M+1)

The compounds of Examples 1, 2, 3, 4, 20, 21, 22, 25, 27, 29, 32 and 81 were synthesized by the same method of Example 23.

Example 24

(R)-N-Neopentyl-6-({[(tetrahydro-2-furyl)methyl]amino}methyl)thiazolo[3,2-a]benzimidazole-2-carboxamide dihydrochloride A DMF (70 ml) solution of the compound of Reference Example 7 (3.10 g) was mixed with 1-hydroxybenzotriazole (1.42 g) and 1-(3-dimethylaminopropyl)-3-ethylcarbodiimide hydrochloride (4.03 g), and the mixture was stirred at room temperature for 2 hours. The reaction mixture was mixed with neopentylamine (2.47 ml) and further stirred at room temperature for 2 hours. After completion of the reaction, the reaction mixture was separated between layers using a mixture of water and ethyl acetate, and the water layer was extracted with ethyl acetate. The organic layer was collected, washed with 5% citric acid aqueous solution, water, 1 M sodium hydroxide aqueous solution, water and saturated brine, dried with anhydrous magnesium sulfate and then concentrated under a reduced pressure. The resulting residue was purified by a column chromatography (eluent; hexane:ethyl acetate=7:3-3:7) to obtain (R)-N-neopentyl-6-({tert-butoxycarbonyl-[(tetrahydro-2-furyl)methyl]amino}methyl)thiazolo[3,2-a]benzimidazole-2-carboxamide (3.40 g). In an ice bath, an ethyl acetate (5 ml) solution of this compound (250 mg) was mixed with 4 M hydrochloric acid-ethyl acetate solution (15 ml) and, after removing the ice bath, stirred for 1 hour. The reaction mixture was dissolved in ethanol and then concentrated under a reduced pressure. By washing the thus obtained crystals with a mixed solvent of ethanol and ethyl acetate, the title compound (175 mg) was obtained.

$^1$H-NMR (DMSO-d$_6$); 0.94 (s, 9H), 1.50-1.60 (m, 1H), 1.77-1.88 (m, 2H), 1.94-2.04 (m, 1H), 2.80-2.89 (m, 1H), 2.97-3.06 (m, 1H), 3.14 (d, 2H), 3.68-3.74 (m, 1H), 3.77-3.83 (m, 1H), 4.15-4.23 (m, 1H), 7.60 (dd, 1H), 7.78 (d, 1H), 8.11 (s, 1H), 8.89-8.96 (m, 1H), 9.34 (s, 1H)

MS (FAB+); 401 (M+1)

The compounds of Examples 48, 49, 50, 52, 53, 55, 57, 58, 59, 69, 70, 72, 73, 77, 78 and 80 were synthesized by the same method of Example 24.

Example 26

6-{[(1,3-Dioxolan-2-ylmethyl)amino]methyl}-N-neopentylthiazolo[3,2-a]benzimidazole-2-carboxamide dihydrochloride A dichloroethane (15 ml) solution of the compound of Reference Example 9 (315 mg) was mixed with acetic acid (285 µl) and 1,3-dioxolan-2-ylmethylamine (282 µl), and the mixture was stirred at room temperature for 1 hour. Subsequently, this was mixed with sodium triacetoxyborohydride (382 mg) and further stirred at room temperature for 1.5 hours. After completion of the reaction, the reaction mixture was mixed with saturated sodium bicarbonate aqueous solution and stirred, and then the insoluble matter was filtered and washed with chloroform. The filtrate and washing solution were combined and concentrated under a reduced pressure, and then the resulting residue was purified by a column chromatography (eluent; chloroform:methanol: 29% aqueous ammonia=100:0:0-93:7:0.7-90:10:1). By making the thus obtained product into hydrochloride in the usual way and recrystallizing it from ethanol and ethyl acetate, the title compound (364 mg) was obtained.

$^1$H-NMR (DMSO-d$_6$); 0.94 (s, 9H), 3.04-3.11 (m, 2H), 3.14 (d, 2H), 3.85-3.92 (m, 2H), 3.96-4.02 (m, 2H), 4.33-4.41 (m, 2H), 5.24 (t, 1H), 7.63 (dd, 1H), 7.79 (d, 1H), 8.15 (d, 1H), 9.07 (t, 1H), 9.46 (s, 1H), 9.64 (br, 2H)

MS (FAB+); 403 (M+1)

Example 28

N-Neopentyl-6-({[(tetrahydro-2H-pyran-4-yl)methyl]amino}methyl)thiazolo[3,2-a]benzimidazole-2-carboxamide dihydrochloride A dichloroethane (15 ml) solution of the compound of Reference Example 9 (315 mg) was mixed with acetic acid (285 µl) and (tetrahydropyran-4-yl)methylamine (346 mg), and the mixture was stirred at room temperature for 2 hours. Subsequently, this was mixed with sodium triacetoxyborohydride (382 mg) and further stirred at room temperature for 1 hour. After completion of the reaction, the reaction mixture was mixed with saturated sodium bicarbonate aqueous solution and stirred, and then the insoluble matter was filtered and washed with chloroform. The filtrate and washing solution were combined and concentrated under a reduced pressure, and then the resulting residue was purified by a column chromatography (eluent; chloroform:methanol: 29% aqueous ammonia=100:0:0-93:7:0.7-90:10:1). By making the thus obtained product into hydrochloride in the usual way and recrystallizing it from ethanol and ethyl acetate, the title compound (260 mg) was obtained.

$^1$H-NMR (DMSO-d$_6$); 0.94 (s, 9H), 1.14-1.26 (m, 2H), 1.70 (d, 2H), 1.95-2.10 (m, 1H), 2.73-2.84 (m, 2H), 3.13 (d, 2H), 3.26 (t, 2H), 3.83 (dd, 2H), 4.32 (br, 2H), 7.67 (br, 1H), 7.96 (br, 1H), 8.46 (br, 1H), 9.01 (br, 1H), 9.52 (br, 3H)

MS (FAB+); 415 (M+1)

Example 31

N-(1,3-Dioxolan-2-ylmethyl)-N-methyl-6-[(oxetan-3-ylamino)methyl]thiazolo[3,2-a]benzimidazole-2-carboxamide A dichloroethane (15 ml) solution of the compound of Reference Example 11 (440 mg) was mixed with acetic acid (362 µl), 3-amino-oxetane hydrochloride (417 mg) and triethylamine (530 µl), and the mixture was stirred at room temperature for 1 hour. Subsequently, this was mixed with sodium triacetoxyborohydride (485 mg) and further stirred at room temperature for 4 hours. After completion of the reaction, the reaction mixture was mixed with saturated sodium bicarbonate aqueous solution and stirred, and then the insoluble matter was filtered and washed with chloroform. The filtrate and washing solution were combined and concentrated under a reduced pressure, and then the resulting residue was purified by a column chromatography (eluent; chloroform:methanol: 29% aqueous ammonia=100:0:0-93:7:0.7-90:10:1). By recrystallizing the formed substance from 2-propanol and diisopropyl ether, the title compound (132 mg) was obtained.

$^1$H-NMR (DMSO-$d_6$); 3.25-4.00 (m, 12H), 4.33 (t, 2H), 4.58 (t, 2H), 5.08 (br, 1H), 7.33 (dd, 1H), 7.61 (d, 1H), 8.05 (br, 1H), 9.01 (br, 1H)

MS (FAB+); 403 (M+1)

The compounds of Examples 30, 33, 36, 38, 40, 41, 42, 43, 44, 45, 46 and 47 were synthesized by the same method of Example 31.

Example 34

N-(1,3-Dioxolan-2-ylmethyl)-N-methyl-6-{[(R)-(tetrahydro-3-furyl)amino]methyl}thiazolo[3,2-a] benzimidazole-2-carboxamide dihydrochloride A dichloroethane (15 ml) solution of the compound of Reference Example 11 (439 mg) was mixed with acetic acid (362 µl), (R)-(tetrahydrofuran-3-yl)amine p-toluenesulfonate (988 mg) and triethylamine (530 µl), and the mixture was stirred at room temperature for 1 hour. Subsequently, this was mixed with sodium triacetoxyborohydride (485 mg) and further stirred at room temperature for 2 hours. After completion of the reaction, the reaction mixture was mixed with saturated sodium bicarbonate aqueous solution and stirred, and then the insoluble matter was filtered and washed with chloroform. The filtrate and washing solution were combined and concentrated under a reduced pressure, and then the resulting residue was purified by a column chromatography (eluent; chloroform:methanol: 29% aqueous ammonia=100:0:0-93:7:0.7-90:10:1). By making the thus obtained product into hydrochloride in the usual way and recrystallizing it from ethanol and ethyl acetate, the title compound (400 mg) was obtained.

$^1$H-NMR (DMSO-$d_6$); 2.10-2.30 (m, 2H), 3.00-4.00 (m, 14H), 4.25-4.35 (m, 2H), 5.09 (br, 1H), 7.76 (d, 1H), 7.81 (d, 1H), 8.36 (s, 1H), 9.20 (br, 1H), 9.95 (br, 2H)

MS (FAB+); 417 (M+1)

Example 35

N-(1,3-Dioxolan-2-ylmethyl)-N-methyl-6-({[((R)-tetrahydro-2-furyl)methyl]amino}methyl)thiazolo[3,2-a]benzimidazole-2-carboxamide dihydrochloride An ethanol (50 ml) solution of the compound of Reference Example 7 (800 mg) was mixed with 4 M hydrochloric acid-ethyl acetate solution (70 ml) and stirred for 3 hours. After completion of the reaction, the reaction mixture was concentrated under a reduced pressure and dried under a reduced pressure, thereby obtaining 6-({[(R)-(tetrahydro-2-furyl)methyl]amino}methyl)thiazolo[3,2-a]benzimidazole-2-carboxamide dihydrochloride (753 mg). A DMF (20 ml) suspension of this compound (375 mg) was mixed with 1-hydroxybenzotriazole (163 mg) and 1-(3-dimethylaminopropyl)-3-ethyl carbodiimide hydrochloride (533 mg), and the mixture was stirred at room temperature for 2 hours. The reaction mixture was mixed with N-(1,3-dioxolan-2-ylmethyl)-N-methylamine (317 µl) and further stirred at room temperature for 2.5 hours. After completion of the reaction, the reaction mixture was poured into water, and the water layer was extracted with ethyl acetate. The organic layer was collected, washed with water and saturated brine, dried with anhydrous sodium sulfate and then concentrated under a reduced pressure. The resulting residue was purified by a column chromatography (eluent; chloroform:methanol=100:0-90:10-85:15). By making the product into hydrochloride in the usual way and recrystallizing it from ethanol and acetonitrile, the title compound (28 mg) was obtained.

$^1$H-NMR (DMSO-$d_6$); 1.51-1.60 (m, 1H), 1.76-1.92 (m, 2H), 1.95-2.04 (m, 1H), 2.84-2.74 (m, 1H), 3.00-3.09 (m, 1H), 3.68-4.01 (m, 11H), 4.15-4.24 (m, 1H), 4.25-4.36 (m, 2H), 5.09 (br, 1H), 7.61 (dd, 1H), 7.76 (d, 1H), 8.20 (br, 1H), 8.95-9.50 (m, 3H)

MS (FAB+); 431 (M+1)

Example 37

N-(1,3-Dioxolan-2-ylmethyl)-6-{[(1,3-dioxolan-2-ylmethyl)amino]methyl}-N-methylthiazolo[3,2-a] benzimidazole-2-carboxamide dihydrochloride A dichloroethane (15 ml) solution of the compound of Reference Example 11 (345 mg) was mixed with acetic acid (285 µl) and 2-aminomethyl-1,3-dioxolan (282 µl), and the mixture was stirred at room temperature for 1 hour. Subsequently, this was mixed with sodium triacetoxyborohydride (382 mg) and further stirred at room temperature for 1.5 hours. After completion of the reaction, the reaction mixture was mixed with saturated sodium bicarbonate aqueous solution and stirred, and then the insoluble matter was filtered and washed with chloroform. The filtrate and washing solution were combined and concentrated under a reduced pressure, and the resulting residue was purified by a column chromatography (eluent; chloroform:methanol: 29% aqueous ammonia=100:0:0-93:7:0.7-90:10:1). By making the product into hydrochloride in the usual way and recrystallizing it from ethanol and ethyl acetate, the title compound (363 mg) was obtained.

$^1$H-NMR (DMSO-$d_6$); 3.06-3.13 (m, 2H), 3.30-4.03 (m, 13H), 4.33 (br, 2H), 5.10 (br, 1H), 5.25 (t, 1H), 7.67 (d, 1H), 7.79 (d, 1H), 8.27 (s, 1H), 9.13 (br, 1H), 9.58 (br, 2H)

MS (FAB+); 433 (M+1)

Example 39

N-(1,3-Dioxolan-2-ylmethyl)-N-methyl-6-({[(tetrahydro-2H-pyran-4-yl)methyl]amino}methyl)thiazolo[3,2-a]benzimidazole-2-carboxamide dihydrochloride A dichloroethane (15 ml) solution of the compound of Reference Example 11 (345 mg) was mixed with acetic acid (285 µl) and (tetrahydropyran-4-yl)methylamine (346 mg), and the mixture was stirred at room temperature for 2 hours. Subsequently, this was mixed with sodium triacetoxyborohydride (382 mg) and further stirred at room temperature for 1 hour. After completion of the reaction, the reaction mixture was mixed with saturated sodium bicarbonate aqueous solution and stirred, and then the insoluble matter was filtered and washed with chloroform. The filtrate and washing solution were combined and concentrated under a reduced pressure, and the resulting residue was purified by a column chromatography (eluent; chloroform:methanol: 29% aqueous ammonia=100:0:0-93:7:0.7-90:10:1). By making the product into hydrochloride in the usual way and recrystallizing it from ethanol and ethyl acetate, the title compound (309 mg) was obtained.

$^1$H-NMR (DMSO-d$_6$); 1.15-1.25 (m, 2H), 1.71 (d, 2H), 1.96-2.10 (m, 1H), 2.76-2.84 (m, 2H), 3.26-4.06 (m, 18 H), 4.25-4.30 (m, 2H), 5.10 (br, 1H), 7.73 (d, 1H), 7.79 (d, 1H), 8.29 (s, 1H), 9.14 (br, 1H), 9.44-9.62 (m, 2H)

MS (FAB+); 445 (M+1)

Example 61

N-(4-Methoxybutyl)-N-methyl-6-({[((R)-tetrahydro-2-furfuryl)methyl]amino}methyl)thiazolo[3,2-a]benzimidazole-2-carboxamide dihydrochloride Example 64

N-(4-Hydroxybutyl)-N-methyl-6-({[((R)-tetrahydro-2-furfuryl)methyl]amino}methyl)thiazolo[3,2-a]benzimidazole-2-carboxamide dihydrochloride A DMF (5 ml) solution of the compound of Reference Example 7 (400 mg) was mixed with 1-hydroxybenzotriazole (163 mg) and 1-(3-dimethylaminopropyl)-3-ethylcarbodiimide hydrochloride (535 mg) and stirred at room temperature for 40 minutes. The reaction mixture was mixed with 4-amino-1-butanol (257 μl) and further stirred at room temperature for 20 minutes. After completion of the reaction, the reaction mixture was separated between layers using a mixture of water and ethyl acetate, and the water layer was extracted with ethyl acetate. The organic layer was collected, washed with water, 1 M sodium hydroxide aqueous solution and saturated brine, dried with anhydrous sodium sulfate and then concentrated under a reduced pressure. The resulting residue was recrystallized from hexane and ethyl acetate to obtain N-(4-hydroxybutyl)-6-({tert-butoxycarbonyl-[((R)-tetrahydro-2-furfuryl)methyl]amino}methyl)thiazolo[3,2-a]benzimidazole-2-carboxamide (380 mg). Under ice-cooling, a DMF (10 ml) solution of this compound (360 mg) was mixed with methyl iodide (223 μl) and sodium hydride (60 to 72%, oily) (52 mg) and stirred under ice-cooling for 1.5 hours. After completion of the reaction, the reaction mixture was poured into saturated sodium bicarbonate aqueous solution and extracted with ethyl acetate. The organic layer was washed with water and saturated brine, dried with anhydrous sodium sulfate and then concentrated under a reduced pressure. The resulting residue was purified by a column chromatography (eluent; chloroform:methanol=100:0-90:10-85:15) to obtain N-(4-methoxybutyl)-N-methyl-6-({tert-butoxycarbonyl-[((R)-tetrahydro-2-furfuryl)methyl]amino}methyl)thiazolo[3,2-a]benzimidazole-2-carboxamide (214 mg) and N-(4-hydroxybutyl)-N-methyl-6-({tert-butoxycarbonyl-[((R)-tetrahydro-2-furfuryl)methyl]amino}methyl)thiazolo[3,2-a]benzimidazole-2-carboxamide (165 mg). At room temperature, an ethanol (10 ml) solution of N-(4-methoxybutyl)-N-methyl-6-({tert-butoxy-carbonyl-[((R)-tetrahydro-2-furfuryl)methyl]amino}methyl)thiazolo[3,2-a]benzimidazole-2-carboxamide (200 mg) was mixed with 4 M hydrochloric acid-ethyl acetate solution (10 ml) and stirred at room temperature for 2 hours. After completion of the reaction, the reaction mixture was concentrated under a reduced pressure. By making the resulting residue in a usual way into hydrochloride and recrystallizing it from ethanol and acetonitrile, the compound of Example 61 (86.0 mg) was obtained.

$^1$H-NMR (DMSO-d$_6$); 1.49-1.70 (m, 5H), 1.76-1.90 (m, 2H), 1.95-2.04 (m, 1H), 2.80-2.92 (m, 1H), 2.98-3.08 (m, 1H), 3.22-3.54 (m, 10H), 3.71 (dd, 1H), 3.80 (dd, 1H), 4.17-4.35 (m, 3H), 7.67 (dd, 1H), 7.77 (d, 1H), 8.25 (br, 1H), 9.06 (br, 1H), 9.34 (br, 1H), 9.67 (br, 1H)

MS (FAB+); 431 (M+1)

In addition, an ethanol (10 ml) solution of N-(4-hydroxybutyl)-N-methyl-6-({tert-butoxycarbonyl-[((R)-tetrahydro-2-furfuryl)methyl]amino}methyl)thiazolo[3,2-a]benzimidazole-2-carboxamide (150 mg) was mixed with 4 M hydrochloric acid-ethyl acetate solution (10 ml) at room temperature and stirred at room temperature for 2 hours. After completion of the reaction, the reaction mixture was concentrated under a reduced pressure. By making the resulting residue into hydrochloride and recrystallizing it from ethanol and acetonitrile, the compound of Example 64 (42.0 mg) was obtained.

$^1$H-NMR (DMSO-d$_6$); 1.41-2.03 (m, 8H), 2.82-2.92 (m, 1H), 2.99-3.08 (m, 1H), 3.35-3.54 (m, 7H), 3.70 (dd, 1H), 3.80 (dd, 1H), 4.19-4.37 (m, 3H), 7.68 (d, 1H), 7.78 (d, 1H), 8.28 (s, 1H), 9.09 (br, 1H), 9.35 (br, 1H), 9.68 (br, 1H)

MS (FAB+); 417 (M+1)

The compounds of Examples 62, 65, 63, 66 and 67 were synthesized by the same methods of Examples 61 and 64.

Example 76

(R)-N-Methyl-N-(2-methyl-2-methylsulfanilpropyl)-6-({[(tetrahydro-2-furyl)methyl]amino}methyl)thiazolo[3,2-a]benzimidazole-2-carboxamide dihydrochloride A DMF (5 ml) solution of (R)-N-(2-Methyl-2-methylsulfanilpropyl)-6-({tert-butoxycarbonyl-[(tetrahydro-2-furyl)methyl]amino}methyl)thiazolo[3,2-a]benzimidazole-2-carboxamide (413 mg), which can be synthesized from the compound of Reference Example 7 and 2-methyl-2-methylsulfanilpropylamine by the same method of Example 24, was mixed with methyl iodide (73 μl) and, in an ice bath, sodium hydride (60 to 72%, oily) (35 mg) was added thereto and stirred in the ice bath for 1 hour. After completion of the reaction, the reaction mixture was poured into saturated sodium bicarbonate aqueous solution and extracted with ethyl acetate. The organic layer was collected, washed with water and then with saturated brine, dried with anhydrous magnesium sulfate and then concentrated under a reduced pressure. The resulting residue was purified by a column chromatography (eluent; hexane:ethyl acetate=75:25-25:75) to obtain (R)-N-methyl-N-(2-methyl-2-methylsulfanilpropyl)-6-({tert-butoxycarbonyl-[(tetrahydro-2-furfuryl)methyl]amino}methyl)thiazolo[3,2-a]benzimidazole-2-carboxamide (398 mg). In an ice bath, ethyl acetate (5 ml) solution of this compound (398 mg) was mixed with 4 M hydrochloric acid-ethyl acetate solution (15 ml) and, after removing the ice bath, stirred for 2 hours. The reaction mixture was dissolved by adding ethanol thereto and then concentrated under a reduced pressure. By recrystallizing the thus obtained crystals from ethanol and ethyl acetate, the title compound (318 mg) was obtained.

$^1$H-NMR (DMSO-d$_6$); 1.29 (s, 6H), 1.51-1.61 (m, 1H), 1.78-1.89 (m, 2H), 1.95-2.09 (m, 4H), 2.81-2.92 (m, 1H), 3.00-3.09 (m, 1H), 3.52 (br, 3H), 3.67-3.74 (m, 3H), 3.77-3.84 (m, 1H), 4.16-4.24 (m, 1H), 4.27-4.33 (m, 2H), 7.65 (dd, 1H), 7.78 (d, 1H), 8.24 (br, 1H), 9.15 (s, 1H)

MS (FAB+); 447 (M+1)

The compounds of Examples 51, 54, 56, 68, 71, 74, 75 and 79, were synthesized by the same method of Example 76.

Structures and physical property values of the aforementioned examples are shown in the following table.

TABLE 1
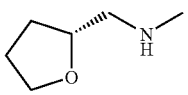
| EX | Ra- | -Rb | Salt | MS |
|---|---|---|---|---|
| 1 | 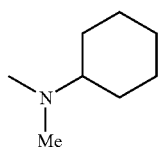 | 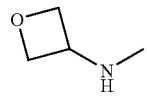 | 2HCl | 427 (M + 1) |
| 2 | 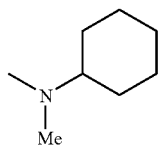 | 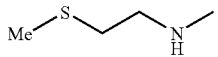 | free | 399 (M + 1) |
| 3 | 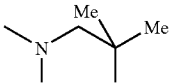 | 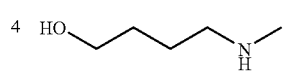 | 2HCl | 405 (M + 1) |
| 4 | 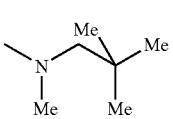 | 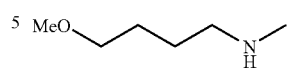 | 2HCl | 403 (M + 1) |
| 5 | 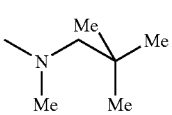 | 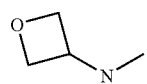 | 2HCl | 417 (M + 1) |
| 6 | 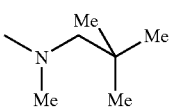 | 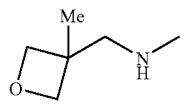 | 1.5 fumarate | 387 (M + 1) |
| 7 | 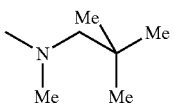 | 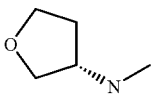 | free | 415 (M + 1) |
| 8 | 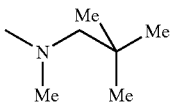 | 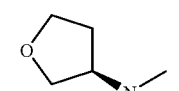 | 2HCl | 401 (M + 1) |
| 9 | 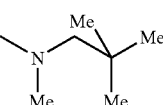 | 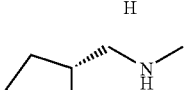 | 2HCl | 401 (M + 1) |
| 10 | 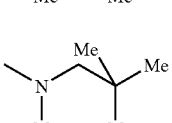 | 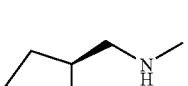 | 2HCl | 415 (M + 1) |
| 11 | 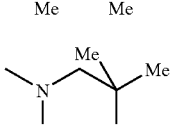 | | 2HCl | 415 (M + 1) |

TABLE 1-continued

[Core structure: Ra-CH2-benzimidazo[2,1-b]thiazole-2-C(=O)-Rb]

| EX | Ra- | -Rb | Salt | MS |
|----|-----|-----|------|-----|
| 12 | (1,3-dioxolan-2-yl)-CH2-N(H)- | -N(Me)CH2C(Me)3 | 2HCl | 417 (M + 1) |
| 13 | ((2S)-tetrahydrofuran-2-yl)-CH2-N(H)- | -N(Me)CH2C(Me)3 | 2HCl | 429 (M + 1) |
| 14 | (1,3-dithiolan-2-yl)-CH2-N(H)- | -N(Me)CH2C(Me)3 | 2HCl | 449 (M + 1) |
| 15 | (tetrahydropyran-4-yl)-N(H)- | -N(Me)CH2C(Me)3 | 2HCl | 415 (M + 1) |
| 16 | (4-MeO-cyclohexyl)-N(H)- | -N(Me)CH2C(Me)3 | 2HCl | 443 (M + 1) |
| 17 | (tetrahydropyran-4-yl)-CH2-N(H)- | -N(Me)CH2C(Me)3 | 2HCl | 429 (M + 1) |
| 18 | (4-MeO-tetrahydropyran-4-yl)-CH2-N(H)- | -N(Me)CH2C(Me)3 | 2HCl | 459 (M + 1) |
| 19 | morpholino-CH2CH2-N(H)- | -N(Me)CH2C(Me)3 | 3HCl | 444 (M + 1) |
| 20 | MeO-CH2CH2-N(H)- | -N(Me)CH2C(Me)3 | 2HCl | 375 (M + 1) |
| 21 | (oxetan-3-yl)-N(H)- | -N(Me)CH2C(Me)3 | free | 373 (M + 1) |
| 22 | ((3S)-tetrahydrofuran-3-yl)-N(H)- | -N(Me)CH2C(Me)3 | 2HCl | 387 (M + 1) |

TABLE 1-continued

| EX | Ra- | -Rb | Salt | MS |
|----|-----|-----|------|-----|
| 23 | (S)-tetrahydrofuran-3-yl-NHMe- | -N(Me)CH2C(Me)3 | 2HCl | 387 (M + 1) |
| 24 | (R)-tetrahydrofuran-2-yl-CH2-NHMe- | -N(Me)CH2C(Me)3 | 2HCl | 401 (M + 1) |
| 25 | (S)-tetrahydrofuran-2-yl-CH2-NHMe- | -N(Me)CH2C(Me)3 | 2HCl | 401 (M + 1) |
| 26 | 1,3-dioxolan-2-yl-CH2-NHMe- | -N(Me)CH2C(Me)3 | 2HCl | 403 (M + 1) |
| 27 | tetrahydropyran-4-yl-NHMe- | -N(Me)CH2C(Me)3 | 2HCl | 401 (M + 1) |
| 28 | tetrahydropyran-4-yl-CH2-NHMe- | -N(Me)CH2C(Me)3 | 2HCl | 415 (M + 1) |
| 29 | morpholin-4-yl-CH2CH2-NHMe- | -N(Me)CH2C(Me)3 | 3HCl | 430 (M + 1) |
| 30 | MeOCH2CH2-NHMe- | -N(Me)CH2-(1,3-dioxolan-2-yl) | 2HCl | 405 (M + 1) |
| 31 | oxetan-3-yl-NHMe- | -N(Me)CH2-(1,3-dioxolan-2-yl) | free | 403 (M + 1) |
| 32 | 3-Me-oxetan-3-yl-CH2-NHMe- | -N(Me)CH2-(1,3-dioxolan-2-yl) | (L)-tartarate | 430 (M + 1) |
| 33 | (S)-tetrahydrofuran-3-yl-NHMe- | -N(Me)CH2-(1,3-dioxolan-2-yl) | 2HCl | 417 (M + 1) |

TABLE 1-continued

| EX | Ra- | -Rb | Salt | MS |
|---|---|---|---|---|
| 34 | tetrahydrofuran-3-yl-N(H)-Me (S) | N(Me)-CH2-1,3-dioxolan-2-yl | 2HCl | 417 (M + 1) |
| 35 | tetrahydrofuran-2-yl-CH2-N(H)- | N(Me)-CH2-1,3-dioxolan-2-yl | 2HCl | 431 (M + 1) |
| 36 | tetrahydrofuran-2-yl-CH2-N(H)- | N(Me)-CH2-1,3-dioxolan-2-yl | 2HCl | 431 (M + 1) |
| 37 | 1,3-dioxolan-2-yl-CH2-N(H)- | N(Me)-CH2-1,3-dioxolan-2-yl | 2HCl | 433 (M + 1) |
| 38 | tetrahydropyran-4-yl-N(H)- | N(Me)-CH2-1,3-dioxolan-2-yl | 2HCl | 431 (M + 1) |
| 39 | tetrahydropyran-4-yl-CH2-N(H)- | N(Me)-CH2-1,3-dioxolan-2-yl | 2HCl | 445 (M + 1) |
| 40 | morpholin-4-yl-CH2CH2-N(H)- | N(Me)-CH2-1,3-dioxolan-2-yl | 3HCl | 460 (M + 1) |
| 41 | oxetan-3-yl-N(H)- | N(H)-CH2-1,3-dioxolan-2-yl | free | 387 (M − 1) FAB(−) |
| 42 | tetrahydrofuran-2-yl-CH2-N(H)- | N(H)-CH2-1,3-dioxolan-2-yl | 2HCl | 417 (M + 1) |
| 43 | tetrahydrofuran-2-yl-CH2-N(H)- | N(H)-CH2-1,3-dioxolan-2-yl | 2HCl | 417 (M + 1) |
| 44 | 1,3-dioxolan-2-yl-CH2-N(H)- | N(H)-CH2-1,3-dioxolan-2-yl | 2HCl | 418 (M)El |
| 45 | tetrahydropyran-4-yl-N(H)- | N(H)-CH2-1,3-dioxolan-2-yl | 2HCl | 416 (M)El |

TABLE 1-continued
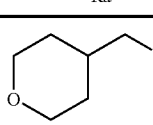
| EX | Ra- | -Rb | Salt | MS |
|---|---|---|---|---|
| 46 | 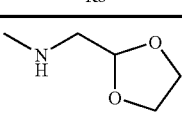 | 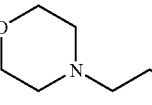 | 2HCl | 431 (M + 1) |
| 47 | 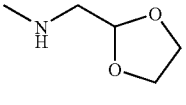 | 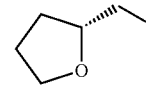 | 3HCl | 446 (M + 1) |
| 48 | 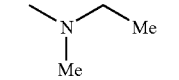 | 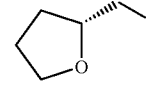 | 2HCl | 373 (M + 1) |
| 49 | 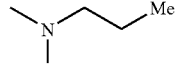 |  | 2HCl | 387 (M + 1) |
| 50 | 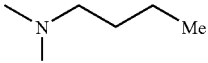 |  | 2HCl | 401 (M + 1) |
| 51 | 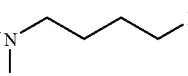 |  | 2HCl | 415 (M + 1) |
| 52 | 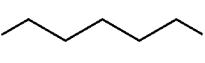 | 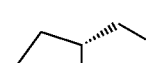 | 2HCl | 429 (M + 1) |
| 53 | 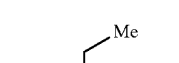 |  | 2HCl | 415 (M + 1) |
| 54 | 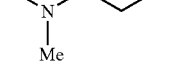 | 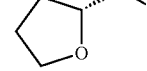 | 2HCl | 415 (M + 1) |
| 55 | 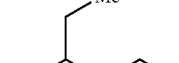 |  | 2HCl | 415 (M + 1) |
| 56 |  | | 2HCl | 415 (M + 1) |

TABLE 1-continued

| EX | Ra- | -Rb | Salt | MS |
|---|---|---|---|---|
| 57 | tetrahydrofuran-2-yl-CH₂-NH-Me | -N(Me)-CH₂CH₂-C(Me)₂-Me | 2HCl | 429 (M + 1) |
| 58 | tetrahydrofuran-2-yl-CH₂-NH-Me | -N(Me)-CH₂-C≡CH | 2HCl | 383 (M + 1) |
| 59 | tetrahydrofuran-2-yl-CH₂-NH-Me | -N(Me)-CH₂CH₂-OMe | 2HCl | 403 (M + 1) |
| 60 | tetrahydrofuran-2-yl-CH₂-NH-Me | -N(Me)-(CH₂)₃-OMe | 2HCl | 417 (M + 1) |
| 61 | tetrahydrofuran-2-yl-CH₂-NH-Me | -N(Me)-(CH₂)₄-OMe | 2HCl | 431 (M + 1) |
| 62 | tetrahydrofuran-2-yl-CH₂-NH-Me | -N(Me)-(CH₂)₅-OMe | 2HCl | 445 (M + 1) |
| 63 | tetrahydrofuran-2-yl-CH₂-NH-Me | -N(Me)-(CH₂)₆-OMe | 2HCl | 459 (M + 1) |
| 64 | tetrahydrofuran-2-yl-CH₂-NH-Me | -N(Me)-(CH₂)₄-OH | 2HCl | 417 (M + 1) |
| 65 | tetrahydrofuran-2-yl-CH₂-NH-Me | -N(Me)-(CH₂)₅-OH | 2HCl | 431 (M + 1) |
| 66 | tetrahydrofuran-2-yl-CH₂-NH-Me | -N(Me)-(CH₂)₆-OH | 2HCl | 445 (M + 1) |
| 67 | tetrahydrofuran-2-yl-CH₂-NH-Me | -N(Me)-(4-OMe-cyclohexyl) | 2HCl | 457 (M + 1) |
| 68 | tetrahydrofuran-2-yl-CH₂-NH-Me | -N(Me)-CH₂-(tetrahydrofuran-2-yl) | 2HCl | 429 (M + 1) |

TABLE 1-continued

| EX | Ra- | -Rb | Salt | MS |
|---|---|---|---|---|
| 69 | tetrahydrofuran-2-ylmethyl-NH- | -N(Me)CH₂CH₂N(Me)Me with extra Me | 3HCl | 416 (M + 1) |
| 70 | tetrahydrofuran-2-ylmethyl-NH- | -N(Me)CH₂CH₂CH₂N(Me)Me | 3HCl | 430 (M + 1) |
| 71 | tetrahydrofuran-2-ylmethyl-NH- | -N(Me)CH₂C(O)NH₂ | 2HCl | 402 (M + 1) |
| 72 | tetrahydrofuran-2-ylmethyl-NH- | -N(Me)CH₂CN | 2HCl | 383 (M + 1) |
| 73 | tetrahydrofuran-2-ylmethyl-NH- | -N(Me)CH₂CH₂CN | 2HCl | 398 (M + 1) |
| 74 | tetrahydrofuran-2-ylmethyl-NH- | -N(Me)CH₂CH₂SMe | 2HCl | 419 (M + 1) |
| 75 | tetrahydrofuran-2-ylmethyl-NH- | -N(Me)CH₂CH₂CH₂SMe | 2HCl | 433 (M + 1) |
| 76 | tetrahydrofuran-2-ylmethyl-NH- | -N(Me)CH₂C(Me)₂SMe | 2HCl | 447 (M + 1) |
| 77 | tetrahydrofuran-2-ylmethyl-NH- | -N(Me)CH₂(1,3-dithiolan-2-yl) | 2HCl | 463 (M + 1) |
| 78 | tetrahydrofuran-2-ylmethyl-NH- | -N(Me)CH₂C(Me)₂SMe | 2HCl | 433 (M + 1) |
| 79 | tetrahydrofuran-2-ylmethyl-NH- | -N(Me)CH₂CF₃ | HCl | 427 (M + 1) |
| 80 | tetrahydrofuran-2-ylmethyl-NH- | -N(CH₂C(Me)₂Me)(CH₂CH₂OMe) | 2HCl | 459 (M + 1) |

TABLE 1-continued

| EX | Ra- | -Rb | Salt | MS |
|---|---|---|---|---|
| 81 | (tetrahydrofuran-2-ylmethylamino-methyl) | N-cyclohexyl-N-methylamide | 2HCl | 427 (M + 1) |

(Test Methods)

1. The mGluR 1 Binding Activity

Effect of the compounds of the invention upon mGluR 1 was verified in accordance with the method described in the Patent Reference 3.

The action of the compounds of the invention was verified by a binding test which uses a tritium-labeled form of 6-amino-N-cyclohexyl-N,3-dimethylthiazolo[3,2-a]benzimidazole-2-carboxamide (specific activity; 81 Ci/mmol (Amersham)) that shows selective and strong action upon mGluR 1.

The aforementioned compound has a high inhibitory activity of $IC_{50}$=24 nM for the reaction of glutamic acid in a phosphatidylinositol (PI) hydrolysis system which uses an mGluR 1 α expression cell (*Nature*, 383, 89-92, 1996).

(Preparation of Rat Cerebellum P2 Membrane Fraction)

Each rat (Wistar, male, 9 to 12 weeks of age) was decapitated to excise the cerebellum. After weight measurement, this was homogenized in 7 to 10 volumes of 0.32 M sucrose solution. After 15 minutes of centrifugation at 900×g, the supernatant was preserved in a container (in ice). The precipitate was again homogenized in 0.32 M sucrose solution of the same volume of the first time and centrifuged at 900×g for 15 minutes. The supernatant obtained this time was combined with the previously obtained supernatant and centrifuged at 15,000×g for 20 minutes. The precipitate was homogenized in 5 mM Tris-HCl, pH 7.4, and centrifuged at 15,000×g for 15 minutes. This step was repeated again. The precipitate was homogenized in 50 mM Tris-HCl, pH 7.4, and centrifuged at 15,000×g for 15 minutes. The precipitate was homogenized in an appropriate amount of 50 mM Tris-HCl, pH 7.4, subdivided into small portions and then preserved at −80° C.

(Binding Test)

As the assay buffer, 50 mM Tris-HCl, 2.5 mM $CaCl_2$, pH 7.4, was used. [$^3$H]-(6-Amino-N-cyclohexyl-N,3-dimethylthiazolo[3,2-a]benzimidazole-2-carboxamide) (specific activity; 81 Ci/mmol; Amersham), a test compound and about 0.1 mg of the rat cerebellum P2 membrane fraction were suspended to a total volume of 100 μl in a 96 well microplate and then incubated at room temperature (about 25° C.) for 45 minutes. Completion of the incubation was carried out by a filtration method using Whatman GF/B filter. Quantity of the radioactivity was measured using a liquid scintillation counter. About 20 nM of [$^3$H]-6-amino-N-cyclohexyl-N,3-dimethylthiazolo[3,2-a]benzimidazole-2-carboxamide was used in the competitive test, and the specific binding was defined as a portion of the total binding, which was replaced by 10 μM of 6-{[(2-methoxyethyl)amino]methyl}-N-neopentylthiazolo[3,2-a]benzimidazole-2-carboxamide (Patent Reference 3, the compound described in Example 75). Evaluation of the test compound was carried out by calculating the ratio of binding inhibition upon the specific binding.

Determination of protein was carried out using BIO-RAD DC protein assay (BIO-RAD). Bovine serum albumin was used as the standard substance.

The results are shown in Table 4.

REFERENCE DOCUMENT

Thomsen C., Mulvihill E. R., Haldeman B., Pickering D. S., Hampson D. R. and Suzdak P. D., A pharmacological characterization of the mGluR 1 alpha subtype of the metabotropic glutamate receptor expressed in a cloned baby hamster kidney cell line., *Brain Res.*, Aug. 13, 1993, 619(1-2), 22-8

2. Inhibitory Effect Upon Neuropathic Pain

1) Streptozotocin (to be Referred to as STZ Hereinafter)—Induced Diabetes Model

The test was carried out by modifying a part of a report (*Pharmacol. Biochem. Behav.*, 39, 541-544, 1991). At a dose of 200 mg/kg, STZ was intraperitoneally administered to each of ICR mice of 4 weeks of age. A preliminary test of a tail pinch test was carried out in the afternoon of the day 2 weeks after the administration, and only animals showing a reaction latency of 3 seconds or less were submitted to the next day's test. Each compound was loaded by 10 mg/kg of oral administration, and the tail pinch test was carried out after 30 minutes of the administration to calculate a difference from the value of latency measured in the preliminary test.

In this connection, normal mice unloaded with STZ show a reaction latency of 6 to 7 seconds in average by this test. STZ-loaded mice having a reaction latency of 3 seconds or less in which distinct reduction in the pain threshold was observed were used in the test of this time.

The results are shown in Table 4. An average reaction latency difference of 2 seconds or more was defined as +

(positive action), and 1.5 seconds or more and less than 2 seconds as ± and less than 1.5 seconds as − (no action).

TABLE 4

| Example | mGluR 1 binding test; IC$_{50}$ (nM) | Dose (p.o.) | Average reaction latency difference |
|---|---|---|---|
| 6 | 2 | 10 mg/kg | + |
| 7 | 9 | 10 mg/kg | + |
| 11 | 3 | 10 mg/kg | + |
| 15 | 26 | 10 mg/kg | + |
| 17 | 6 | 10 mg/kg | + |
| 23 | 30 | 10 mg/kg | + |
| 24 | 11 | 10 mg/kg | + |
| 26 | 8 | 10 mg/kg | + |
| 28 | 48 | 10 mg/kg | + |
| 31 | 43 | 10 mg/kg | + |
| 34 | 37 | 10 mg/kg | + |
| 35 | 12 | 10 mg/kg | + |
| 37 | 8 | 10 mg/kg | + |
| 39 | 26 | 10 mg/kg | + |
| Control compd. A | 22 | 100 mg/kg | − |
| Control compd. B | 25 | 100 mg/kg | − |
| Control compd. C | 7 | 100 mg/kg | − |
| Control compd. D | 25 | 100 mg/kg | − |

Control compound. A: Patent Reference 4, the compound disclosed in Example 112

Control compound. B: Patent Reference 4, the compound disclosed in Example 116

Control compound. C: Patent Reference 4, the compound disclosed in Example 126

Control compound. D: Patent Reference 4, the compound disclosed in Example 133

Based on the above tests, it was confirmed that the compounds of the invention are compounds which specifically bind to mGluR 1.

Also, it was confirmed that the compounds of the invention have the effect to treat diabetes mellitus-induced neuropathic pain by their oral administration.

In addition, it was confirmed that the compounds of the invention are compounds whose oral activity is 10 times or more superior to the control compounds having analogous structures but no aniline amino group and therefore are compounds useful as oral preparations.

2) L5/L6 Spinal Nerves-Ligated Rat

The test was carried out by modifying a part of a report (*PAIN*, 50, 355-363, 1992). Using SD rats, left side hip nerves (L5 and L6) were ligated with a silk thread under pentobarbital anesthesia. The following test was carried out during a period of from on the 7th day to the 14th day after the operation.

Each compound was orally administered, and the von Frey hair (VFH) test was carried out 30 minutes thereafter to calculate the pain threshold value against mechanical nocuous stimulus. The measurement was carried out on the left and right hind legs.

In this connection, there was no difference in the pain threshold value of pseudo-operation rats between left and right hind legs, which was 17-20 g (log (g):1.23-1.30, and reduction of the pain threshold value against mechanical nocuous stimulus was observed in the operated side leg of the L5/L6 spinal nerves-ligated rat.

The significant difference test was carried out using the Dunnett method on respective left and right legs between the control group and compound-administered group.

Results

The compounds of Examples 15, 17 and 28 showed their efficacy upon the threshold value reduction in the operated side by 30 mg/kg of oral administration.

It was confirmed based on this that the compounds having mGluR 1 antagonism have a therapeutic effect for a neuropathic pain caused by nerve compression.

3. Genetic Toxicity

Gene mutation inducing ability of the compounds of the invention was verified by a reverse mutation test which uses a bacterium.

The test was carried out in accordance with the genetic toxicity test guideline of drugs (Iyakushin No. 1604, Nov. 1, 1999) by a pre-incubation method in the presence and absence of a metabolic activation system. However, *Salmonella typhimurium* TA 98 and TA 100 alone were used as the test strains.

(Reverse Mutation Test Using a Bacterium)

A 0.5 ml portion of 0.1 M sodium phosphate buffer (pH 7.4), 0.1 ml of an overnight-cultured test strain suspension and 0.1 ml of a solution of a substance to be tested were put into a test tube and shaken (60 reciprocation/min) at 37° C. for 20 minutes, and then 2 ml of soft agar kept at about 45° C. was added thereto and the mixture was spread on a minimal glucose agar plate medium (plate) and cultured at 37° C. for about 48 hours. In the case of the metabolic activation test, the same procedure was carried out by adding the same volume of S9Mix instead of the 0.1 M sodium phosphate buffer.

Results

The S9Mix used in the metabolic activation test was prepared using S-9/cofactor A set (a 9,000×g supernatant of homogenate of the rat liver in which drug metabolizing enzymes had been induced using phenobarbital and 5,6-benzoflavone and Cofactor, for Ames test use, Oriental Yeast Co., Ltd.). The amount of S9 in S9Mix was set to 0.1 ml/ml. Dimethyl sulfate was used as the solvent.

The number of colonies formed on the plate after 48 hours of culturing was counted. When the number of reverse mutation colonies (average value) on the plate treated with a substance to be tested was increased to 2 times or more of the number of the solvent control reverse mutation colonies (average value), and its dose-dependency was observed and the reproducibility was confirmed, it was judged that the compound has the gene mutation inducing ability.

While the aniline amino group-containing compounds A and B described in the Patent Reference 2 have the oral activity equivalent to the compounds of the invention (cf. Patent Reference 2), it was confirmed as a result of the above test that the compound A is positive in gene mutation inducing ability.

On the other hand, it was confirmed that the compound of Example 12 of the invention has an oral activity similar to or larger than that of the compounds described in the Patent Reference 2 (effective at 10 mg/kg), and its gene mutation inducing ability is also negative.

Accordingly, it was confirmed that the compounds of the invention are clinically useful compounds, because they have excellent oral activity and do not have gene mutation inducing ability.

INDUSTRIAL APPLICABILITY

The compounds of the invention are compounds useful as medicaments, because they are compounds which have excellent oral activity showing strong action upon the metabotropic glutamate receptor and also have excellent therapeutic effect upon diabetic and nerve compression-induced neuropathic pain. In addition, the compounds of the invention are clinically useful, because they are compounds which do not have aniline amino group and in which improvement of oral activity was achieved so that they do not have gene mutation inducing ability based on the aniline amino group.

Accordingly, the compounds of the invention are useful as preventive or therapeutic agents for diseases in which the mGluR 1 receptor is considered to be taking a role, such as epilepsy, pain, inhibition of nerve cell death, benzodiazepine withdrawal syndrome, Parkinson disease, migraine, anxiety disorder, cerebral infarction (preferably an agent for preventing development of infarct focus, which is administered acute phase of cerebral infarction) and a neuropathic pain (preferably a pain accompanied by diabetic neuropathy, a neuralgia after shingles, a cancerous pain or a postoperative chronic pain).

What is claimed is:

1. An aminomethyl-substituted thiazolobenzimidazole compound represented by the following formula (I) or a salt thereof

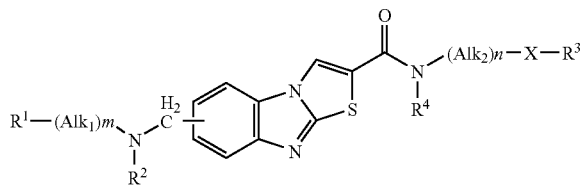

(I)

(wherein signs in the formula mean as follows;

$R^1$: an oxygen-containing saturated hetero ring- which may be substituted,

Alk1: a lower alkylene, m: 0 or 1,

Alk2: a lower alkylene which may be substituted with oxo group, n: 0 or 1,

X: a bond, O, S or $NR^5$, $R^3$: a lower alkyl or a saturated hetero ring-, and $R^2$, $R^4$ and $R^5$: the same or different from one another and each represents H or lower alkyl, with the proviso that $R^3$ does not represent a lower alkyl when X is a bond and n is 1).

2. A compound selected from the group consisting of N-methyl-N-neopentyl-6-[(oxetan-3-ylamino)methyl]thiazolo[3,2-a]benzimidazole-2-carboxamide; 6-{[(1,3-dioxolan-2-ylmethyl)amino]methyl}-N-methyl-N-neopentylthiazolo[3,2-a]benzimidazole-2-carboxamide; and N-neopentyl-6-({[tetrahydro-2H-pyran-4-yl)methyl]amino}methyl)thiazolo[3,2-a]benzimidazole-2-carboxamide; or a salt thereof.

3. A medicament which comprises the aminomethyl-substituted thiazolobenzimidazole compound described in claim 1 or a salt thereof as the active ingredient.

* * * * *

UNITED STATES PATENT AND TRADEMARK OFFICE
CERTIFICATE OF CORRECTION

PATENT NO. : 7,250,429 B2
APPLICATION NO. : 10/508329
DATED : July 31, 2007
INVENTOR(S) : Hirotsune Itahana et al.

It is certified that error appears in the above-identified patent and that said Letters Patent is hereby corrected as shown below:

Please amend column 17, lines 46-47 as follows:

N-Methyl-N-neopentyl-6-({[((R)-tetrahydro-2-~~fur~~furyl)methyl]amino}methyl)thiazolo[3,2-a]benzimida-

Please amend column 18, lines 9-10 as follows:

N-Methyl-N-neopentyl-6-({[((S)-tetrahydro-2-~~fur~~furyl)methyl]amino}methyl)thiazolo[3,2-a]benzimida-

Please amend column 19, line 29 as follows:

2-~~fur~~furyl)methyl]amino}methyl)thiazolo[3,2-a]

Please amend column 23, line 65 as follows:

2-~~carboxamide~~carboxylic acid dihydrochloride (753 mg). A DMF (20 ml)

Please amend column 25, line 16 as follows:

2-~~fur~~furyl)methyl]amino}methyl)thiazolo[3,2-a]

Please amend column 25, line 22 as follows:

2-~~fur~~furyl)methyl]amino}methyl)thiazolo[3,2-a]

Please amend column 25, line 40 as follows:

butoxycarbonyl-[((R)-tetrahydro-2-~~fur~~furyl)methyl]

Please amend column 25, line 53 as follows:

rahydro-2-~~fur~~furyl)methyl]amino}methyl)thiazolo[3,2-a]

UNITED STATES PATENT AND TRADEMARK OFFICE
CERTIFICATE OF CORRECTION

PATENT NO. : 7,250,429 B2
APPLICATION NO. : 10/508329
DATED : July 31, 2007
INVENTOR(S) : Hirotsune Itahana et al.

It is certified that error appears in the above-identified patent and that said Letters Patent is hereby corrected as shown below:

Please amend column 25, line 56 as follows:

tetrahydro-2-~~fur~~furyl)methyl]amino}methyl)thiazolo[3,2-a]

Please amend column 25, line 60 as follows:

2-~~fur~~furyl)methyl]amino}methyl)thiazolo[3,2-a]benzimida-

Please amend column 26, line 9 as follows:

2-~~fur~~furyl)methyl]amino}methyl)thiazolo[3,2-a]benzimida-

Please amend column 26, line 27 as follows:

(R)-N-Methyl-N-(2-methyl-2-methylsulfani~y~lpropyl)-

Please amend column 26, lines 32-33 as follows:

A DMF (5 ml) solution of (R)-N-(2-Methyl-2-methylsulfani~y~lpropyl)-6-({tert-butoxycarbonyl-[(tetrahydro-2-furyl)

Please amend column 26, line 37 as follows:

ylsulfan~i~ylpropylamine by the same method of Example 24,

Please amend column 26, lines 47-48 as follows:

to obtain (R)-N-~~m~~ethyl-N-(2-methyl-2-methylsulfan~i~ylpropyl)-6-({tert-butoxycarbonyl-[(tetrahydro-2-furfuryl)me-

UNITED STATES PATENT AND TRADEMARK OFFICE
CERTIFICATE OF CORRECTION

PATENT NO.       : 7,250,429 B2
APPLICATION NO.  : 10/508329
DATED            : July 31, 2007
INVENTOR(S)      : Hirotsune Itahana et al.

It is certified that error appears in the above-identified patent and that said Letters Patent is hereby corrected as shown below:

Please replace columns 29 and 30, compounds 20-22 with the following amended columns:

| 20 | 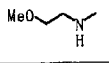 | 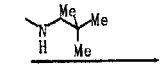 | 2HCl | 375 (M+1) |
|---|---|---|---|---|
| 21 | 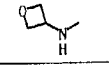 | 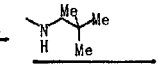 | free | 373 (M+1) |
| 22 | 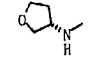 | 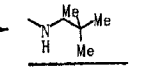 | 2HCl | 387 (M+1) |

Please replace columns 31 and 32, compounds 23-26 with the following amended columns:

| 23 | 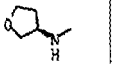 | 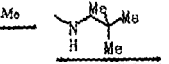 | 2HCl | 387 (M+1) |
|---|---|---|---|---|
| 24 | 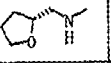 | 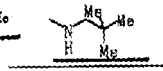 | 2HCl | 401 (M+1) |
| 25 | 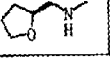 | 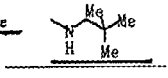 | 2HCl | 401 (M+1) |
| 26 | 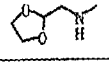 | 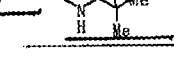 | 2HCl | 403 (M+1) |

UNITED STATES PATENT AND TRADEMARK OFFICE
CERTIFICATE OF CORRECTION

PATENT NO. : 7,250,429 B2
APPLICATION NO. : 10/508329
DATED : July 31, 2007
INVENTOR(S) : Hirotsune Itahana et al.

It is certified that error appears in the above-identified patent and that said Letters Patent is hereby corrected as shown below:

Please replace columns 31 and 32, compounds 27-29 with the following amended columns:

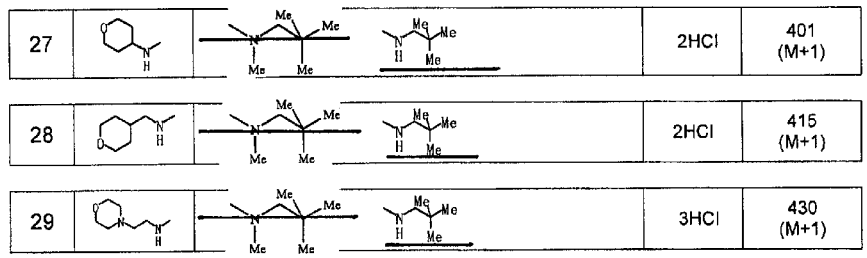

Please replace columns 35-36, compound 54 with the following amended columns:

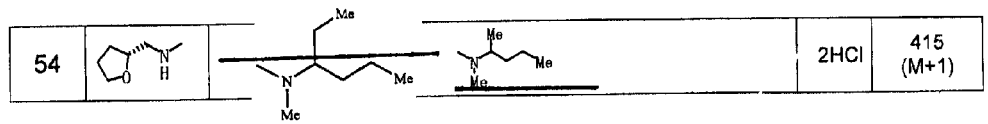

Please replace columns 39-40, compound 78 with the following amended columns:

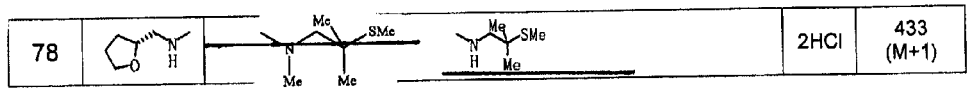

UNITED STATES PATENT AND TRADEMARK OFFICE
CERTIFICATE OF CORRECTION

PATENT NO. : 7,250,429 B2
APPLICATION NO. : 10/508329
DATED : July 31, 2007
INVENTOR(S) : Hirotsune Itahana et al.

It is certified that error appears in the above-identified patent and that said Letters Patent is hereby corrected as shown below:

Please amend column 46, line 23 as follows:

N-neopentyl-6-({[(tetrahydro-2H-pyran-4-yl)methyl]

Signed and Sealed this

Twenty-fifth Day of March, 2008

JON W. DUDAS
*Director of the United States Patent and Trademark Office*